(12) United States Patent
Sundermann et al.

(10) Patent No.: US 7,439,394 B2
(45) Date of Patent: Oct. 21, 2008

(54) CYCLOHEXYL-1,4-DIAMINE COMPOUNDS

(75) Inventors: Corinna Sundermann, Aachen (DE); Bernd Sundermann, Aachen (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 11/594,944

(22) Filed: Nov. 9, 2006

(65) Prior Publication Data

US 2007/0117803 A1    May 24, 2007

Related U.S. Application Data

(63) Continuation of application No. PCT/EP2005/004910, filed on May 6, 2005.

(30) Foreign Application Priority Data

May 10, 1924   (DE) .................. 10 2004 023 508

(51) Int. Cl.
 *C07C 233/00* (2006.01)
 *A61K 31/16* (2006.01)
(52) U.S. Cl. ............... 564/123; 564/138; 564/141; 564/152; 564/154; 564/155; 564/161; 564/192; 514/613; 514/617; 514/625
(58) Field of Classification Search ................ None
See application file for complete search history.

(56) References Cited

FOREIGN PATENT DOCUMENTS

WO    WO 02/089783 A    11/2002

OTHER PUBLICATIONS

Database CAPLUS on STN, Acc. No. 2004:17853, Yasuda et al., JP 2004002368 (Jan. 8, 2004) (abstract).*

* cited by examiner

*Primary Examiner*—Brian J Davis
(74) *Attorney, Agent, or Firm*—Crowell & Moring LLP

(57) ABSTRACT

Novel cyclohexyl-1,4-diamine compounds corresponding to formula I,

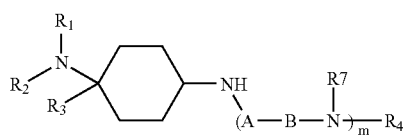

processes for the production thereof, pharmaceutical compositions containing these compounds, methods of producing pharmaceutical compositions including these compounds and related methods of treating or inhibiting certain diseases or conditions.

31 Claims, No Drawings

CYCLOHEXYL-1,4-DIAMINE COMPOUNDS

CROSS-REFERENCE TO RELATED APPLICATIONS

This application is a continuation of International patent application Ser. No. PCT/EP2005/004910 filed May 6, 2005 which claims benefit to German patent application Serial No. 10 2004 023 508.2 filed May 10, 2004, the entire disclosures of which are hereby incorporated in their entirety.

FIELD OF THE INVENTION

The present invention relates to substituted cyclohexyl-1,4-diamine compounds, processes for the production thereof, pharmaceutical compositions containing these compounds, methods of producing pharmaceutical compositions including these compounds and related methods of treating or inhibiting certain diseases or conditions.

BACKGROUND OF THE INVENTION

The treatment of chronic and non-chronic pain is of great importance in medicine. There is a worldwide need for highly effective therapies for pain. The urgent need for action for a treatment for pain that is fair to the patient and targeted, which is to be understood as meaning the successful and satisfactory treatment of pain for the patient, is documented in the large number of scientific works that have recently appeared in the field of applied analgesia or fundamental research into nociception.

Conventional µ-opioids such as morphine are highly effective in the therapy of strong to very strong pain and are of great importance in the therapy of pain. However, it can be advantageous to influence other opioid receptors, in particular the ORL-1 receptor, in addition to the µ-opioid receptor, because the pure µ-opioids also exhibit undesirable side-effects, such as constipation and respiratory depression, and can also lead to dependency. The opioid receptors δ, κ and ORL-1 are also involved in the occurrence of pain (Opioids: Introduction, p. 127-150, Further Opioid Receptors, 455-476 in: Analgesics—From Chemistry and Pharmacology to Clinical Application, Wiley VCH, 2002).

It is also known that influencing serotonin and/or noradrenaline reuptake can have an advantageous effect on the spectrum of action and side-effects of opioids (example: tramadol, see Opioids with Clinical Relevance: Tramadol, 228-230 in: Analgesics—From Chemistry and Pharmacology to Clinical Application, Wiley VCH 2002).

The ORL1 receptor is additionally also involved in the regulation of further physiological and pathophysiological processes. These include inter alia learning and memory formation (Manabe et al., Nature, 394, 1997, p. 577-581), hearing ability (Nishi et al., EMBO J., 16, 1997, p. 1858-1864) and numerous further processes. In an overview article by Calo et al. (Br. J. Pharmacol., 129, 2000, 1261-1283), an overview is given of the indications or biological processes in which the ORL1 receptor plays or with high probability might play a role. Those mentioned are, inter alia: analgesia, stimulation and regulation of food intake, influence on µ-agonists such as morphine, treatment of withdrawal symptoms, reduction of the addictive potential of opioids, anxiolysis, modulation of motor activity, memory disorders, epilepsy; modulation of neurotransmitter secretion, in particular of glutamate, serotonin and dopamine, and therefore neurodegenerative diseases; influencing of the cardiovascular system, initiation of an erection, diuresis, antinatriuresis, electrolyte balance, arterial blood pressure, water retention diseases, intestinal motility (diarrhoea), relaxing effects on the respiratory tract, micturition reflex (urinary incontinence). The use of agonists and antagonists as anoretics, analgesics (also in co-administration with opioids) or nootropics is furthermore discussed.

From the prior art (WO 02090317) there are known structurally related compounds that have an affinity for the ORL-1 receptor. No influence on noradrenaline and serotonin reuptake has hitherto been described for this structural class.

SUMMARY OF THE INVENTION

The object of the present invention was to provide pharmaceutical formulations that act on the opioid receptor system and accordingly are suitable for medicaments for the treatment in particular of the various diseases associated with this system according to the prior art or for use in the indications mentioned therein. The compounds should additionally influence noradrenaline and serotonin reuptake.

The invention accordingly provides substituted cyclohexyl-1,4-diamine derivatives of the general formula I

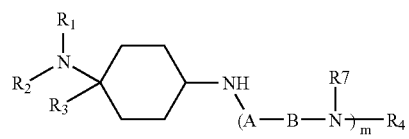

wherein $R^1$ and $R^2$, independently of one another, represent H; $C_{1-5}$-alkyl, in each case saturated or unsaturated, branched or unbranched, mono- or poly-substituted or unsubstituted; $C_{3-8}$-cycloalkyl, in each case mono- or poly-substituted or unsubstituted; or aryl, $C_{3-8}$-cycloalkyl or heteroaryl bonded via $C_{1-3}$-alkyl, in each case mono- or poly-substituted or unsubstituted;

or the radicals $R^1$ and $R^2$ together represent $CH_2CH_2OCH_2CH_2$, $CH_2CH_2NR^{10}CH_2CH_2$ or $(CH_2)_{3-6}$,
wherein $R^{10}$ represents H; $C_{1-5}$-alkyl, in each case saturated or unsaturated, branched or unbranched, mono- or poly-substituted or unsubstituted; $C_{3-8}$-cycloalkyl, in each case mono- or poly-substituted or unsubstituted; aryl or heteroaryl, in each case mono- or poly-substituted or unsubstituted; or aryl, $C_{3-8}$-cycloalkyl or heteroaryl bonded via $C_{1-3}$-alkyl, in each case mono- or poly-substituted or unsubstituted; C(O)phenyl, C(O)heteroaryl, C(O)$C_{1-5}$-alkyl, in each case substituted or unsubstituted;

$R^3$ represents $C_{1-5}$-alkyl, in each case saturated or unsaturated, branched or unbranched, mono- or poly-substituted or unsubstituted; $C_{3-8}$-cycloalkyl, in each case mono- or poly-substituted or unsubstituted; aryl or heteroaryl, in each case unsubstituted or mono- or poly-substituted; aryl, heteroaryl or $C_{3-8}$-cycloalkyl bonded via a $C_{1-3}$-alkyl group, in each case unsubstituted or mono- or poly-substituted;

m represents 1, 2 or 3;

A represents C(O) or $SO_2$;

B represents $(CR^5R^6)_n$ or aryl, heteroaryl or $C_{3-8}$-cycloalkyl, in each case mono- or poly-substituted or unsubstituted; or aryl, $C_{3-8}$-cycloalkyl or heteroaryl bonded via $C_{1-3}$-alkyl (wherein an individual carbon atom of the alkyl chain may also be replaced by O), in each case mono- or poly-substituted or unsubstituted, wherein the $C_{1-3}$-alkyl chain may link the cyclic radical to A and/or N, that is to say two alkyl chains are optionally present; where n=1, 2, 3, 4 or 5;

$R^4$ represents $C(O)R^9$ or $SO_2R^8$;

$R^5$, $R^6$ represent H, $C_{1-5}$-alkyl, in each case saturated or unsaturated, branched or unbranched, mono- or poly-substituted or unsubstituted; $C_{3-8}$-cycloalkyl, in each case mono- or poly-substituted or unsubstituted; aryl or heteroaryl, in each case mono- or poly-substituted or unsubstituted; or aryl, $C_{3-8}$-cycloalkyl or heteroaryl bonded via $C_{1-3}$-alkyl, in each case mono- or poly-substituted or unsubstituted;

$R^7$ represents H or, with B, forms a five-, six- or seven-membered ring which may be saturated or unsaturated but not aromatic and which may be part of a polycyclic system;

$R^8$ represents $C_{1-5}$-alkyl, in each case saturated or unsaturated, branched or unbranched, mono- or poly-substituted or unsubstituted; $C_{3-8}$-cycloalkyl, in each case mono- or poly-substituted or unsubstituted; aryl or heteroaryl, in each case mono- or poly-substituted or unsubstituted; or aryl, $C_{3-8}$-cycloalkyl or heteroaryl bonded via $C_{1-3}$-alkyl, in each case mono- or poly-substituted or unsubstituted;

$R^9$ represents $OR^{11}$, $C_{1-5}$-alkyl, in each case saturated or unsaturated, branched or unbranched, mono- or poly-substituted or unsubstituted; $C_{3-8}$-cycloalkyl, in each case mono- or poly-substituted or unsubstituted; aryl or heteroaryl, in each case mono- or poly-substituted or unsubstituted; or aryl, $C_{3-8}$-cycloalkyl or heteroaryl bonded via $C_{1-3}$-alkyl, in each case mono- or poly-substituted or unsubstituted;

$R^{11}$ represents $C_{1-5}$-alkyl, in each case saturated or unsaturated, branched or unbranched, mono- or poly-substituted or unsubstituted; $C_{3-8}$-cycloalkyl, in each case mono- or poly-substituted or unsubstituted; aryl or heteroaryl, in each case mono- or poly-substituted or unsubstituted; or aryl, $C_{3-8}$-cycloalkyl or heteroaryl bonded via $C_{1-3}$-alkyl, in each case mono- or poly-substituted or unsubstituted;

in the form of the racemate; in the form of the enantiomers, diastereoisomers, mixtures of the enantiomers or diastereoisomers or in the form of an individual enantiomer or diastereoisomer; in the form of the bases and/or salts of physiologically acceptable acids or cations.

When different radicals, for example R5 and R6, are combined, and also when the same substituents are named several times by the addition of a numerator, e.g. (CR5R6)n, a substituent can assume different meanings for two or more radicals, for example R5 and/or R6, within a substance.

The compounds according to the invention exhibit good binding to the μ receptor and the ORL-1 receptor, as well as to other opioid receptors. Surprisingly, it has been found that the compounds are also good inhibitors of noradrenaline and serotonin reuptake. They are accordingly suitable also for the treatment of depression and/or bulimia and/or anorexia and/or catalepsy and/or for anxiolysis and/or for increasing vigilance and/or libido.

The expressions "C1-5-alkyl" and "C1-3-alkyl" within the scope of this invention include acyclic saturated or unsaturated hydrocarbon radicals which may be branched- or straight-chained as well as unsubstituted or mono- or poly-substituted and which have 1, 2, 3, 4 or 5 carbon atoms and 1, 2 or 3 carbon atoms, respectively, i.e. C1-5-alkanyls, C2-5-alkenyls and C2-5-alkynyls, and C1-3-alkanyls, C2-3-alkenyls and C2-3-alkynyls. Alkenyls have at least one C—C double bond and alkynyls have at least one C—C triple bond. Alkyl is advantageously selected from the group comprising methyl, ethyl, n-propyl, 2-propyl, n-butyl, isobutyl, sec.-butyl, tert.-butyl, n-pentyl, isopentyl, neopentyl, ethylenyl (vinyl), ethynyl, propenyl (—CH2CH═CH2, —CH═CH—CH3, —C(═CH2)—CH3), propynyl (—CH—C≡CH, —C≡C—CH3), 1,1-dimethylethyl, 1,1-dimethylpropyl, butenyl, butynyl, pentenyl and pentynyl.

For the purposes of this invention, the expression "cycloalkyl" or "C3-8-cycloalkyl" denotes cyclic hydrocarbons having 3, 4, 5, 6, 7 or 8 carbon atoms, wherein the hydrocarbons may be saturated or unsaturated (but not aromatic), unsubstituted or mono- or poly-substituted. With regard to cycloalkyl, the term also includes saturated or unsaturated (but not aromatic) cycloalkyls in which one or two carbon atoms have been replaced by a hetero atom S, N or O. C3-8-Cycloalkyl is advantageously selected from the group containing cyclopropyl, cyclobutyl, cyclopentyl, cyclohexyl, cycloheptyl, cyclooctyl, cyclopentenyl, cyclohexenyl, cycloheptenyl and cyclooctenyl, but also tetrahydropyranyl, dioxanyl, dioxolanyl, morpholinyl, piperidinyl, piperazinyl, pyrazolinonyl and pyrrolidinyl.

The term (CH2)3-6 is to be understood as meaning —CH2-CH2-CH2-, —CH2-CH2-CH2-CH2-, —CH2-CH2-CH2-CH2-CH2- and —CH2-CH2-CH2-CH2-CH2-CH2-.

Within the scope of this invention, the expression "aryl" denotes carbocyclic ring systems having at least one aromatic ring but without hetero atoms in even one of the rings, inter alia phenyls, naphthyls and phenanthrenyls, fluoranthenyls, fluorenyls, indanyls and tetralinyls. The aryl radicals may also be condensed with further saturated, (partially) unsaturated or aromatic ring systems. Each aryl radical may be present in unsubstituted or mono- or poly-substituted form, it being possible for the aryl substituents to be identical or different and to be in any desired and possible position of the aryl. Phenyl or naphthyl radicals are particularly advantageous.

The expression "heteroaryl" denotes a 5-, 6- or 7-membered cyclic aromatic radical which contains at least one, optionally 2, 3, 4 or 5, hetero atoms, the hetero atoms being identical or different and the heterocyclic ring being unsubstituted or mono- or poly-substituted; in the case of substitution on the heterocyclic ring, the substituents may be identical or different and may be in any desired and possible position of the heteroaryl. The heterocyclic ring may also be part of a bi- or poly-cyclic system. Preferred hetero atoms are nitrogen, oxygen and sulfur. It is preferable for the heteroaryl radical to be selected from the group containing pyrrolyl, indolyl, furyl (furanyl), benzofuranyl, thienyl (thiophenyl), benzothienyl, benzothiadiazolyl, benzothiazolyl, benzotriazolyl, benzodioxolanyl, benzodioxanyl, phthalazinyl, pyrazolyl, imidazolyl, thiazolyl, oxazolyl, isoxazolyl, pyrrolyl, pyridinyl, pyridazinyl, pyrimidinyl, pyrazinyl, pyranyl, indazolyl, purinyl, indolizinyl, quinolinyl, isoquinolinyl, isothiazolyl, imidazolyl, triazolyl, triazinyl, quinazolinyl, carbazolyl, phenazinyl, phenothiazinyl or oxadiazolyl, it being possible for the bond to the compounds of the general structure I to be effected via any desired and possible ring member of the heteroaryl radical.

In connection with "alkyl", the term "substituted" within the scope of this invention is understood as meaning the substitution of one or more hydrogen radicals by F, Cl, Br, I, —CN, ═O, ═S, NH2, NH-alkyl, NH-aryl, NH-heteroaryl, NH-cycloalkyl, NH-alkyl-aryl, NH-alkyl-heteroaryl, NH-alkyl-OH, N(alkyl)2, N(alkyl-aryl)2, N(alkyl-heteroaryl)2, N(cycloalkyl)2, N(alkyl-OH)2, NH(C═O)alkyl, NH(C═O)aryl, NO2, SH, S-alkyl, S-aryl, S-heteroaryl, S-alkyl-aryl, S-alkyl-heteroaryl, S-cycloalkyl, S-alkyl-OH, S-alkyl-SH, OH, O-alkyl, O-aryl, O-heteroaryl, O-alkyl-aryl, O-alkyl-heteroaryl, O-cycloalkyl, O-alkylcycloalkyl, O-alkyl-OH, CHO, C(═O)C1-6-alkyl, C(═S)C1-6-alkyl, C(═O)aryl, C(═S)aryl, C(═O)C1-6-alkyl-aryl, C(═S)C1-6-alkyl-aryl, C(═O)-heteroaryl, C(═S)-heteroaryl, C(=O)-cycloalkyl, C(=S)-cycloalkyl, CO2H, CO2-alkyl, CO2-alkyl-aryl, C(=O)NH2, C(=O)NH-alkyl, C(=O)NH-aryl, C(=O)NH-cycloalkyl, C(=O)N(alkyl)2, C(=O)N(alkyl-aryl)2, C(=O)N(alkyl-heteroaryl)2, C(=O)N(cycloalkyl)2, SO-alkyl, SO2-alkyl, SO2NH2, SO3H, PO(O—C1-6-alkyl)2, cycloalkyl, aryl or heteroaryl, polysubstituted radicals being understood to be those radicals that are polysubstituted, e.g. di- or tri-substituted, either on different or on the same atoms, for example trisubstituted on the same carbon atom, as in the case of CF3 or —CH2CF3, or in different positions, as in the case of —CH(OH)—CH=CH—CHCl2. Polysubstitution can be effected with the same substituent or with different substituents. It is also possible for a substituent itself to be substituted; for example, —Oalkyl includes inter alia also —O—CH2-CH2-O—CH2-CH2-OH.

In relation to "aryl", "heteroaryl" and "cycloalkyl", "mono- or poly-substituted" within the scope of this invention is understood as meaning the mono- or poly-substitution, for example the di-, tri-, tetra- or penta-substitution, of one or more hydrogen atoms of the ring system by F, Cl, Br, I, CN, NH2, NH-alkyl, NH-aryl, NH-heteroaryl, NH-alkyl-aryl, NH-alkyl-heteroaryl, NH-cycloalkyl, NH-alkyl-OH, N(alkyl)2, N(alkyl-aryl)2, N(alkyl-heteroaryl)2, N(cycloalkyl)2, N(alkyl-OH)2, NO2, SH, S-alkyl, S-cycloalkyl, S-aryl, S-heteroaryl, S-alkyl-aryl, S-alkyl-heteroaryl, S-cycloalkyl, S-alkyl-OH, S-alkyl-SH, OH, O-alkyl, O-cycloalkyl, O-aryl, O-heteroaryl, O-alkyl-aryl, O-alkyl-heteroaryl, O-alkyl-OH, CHO, C(=O)C1-6-alkyl, C(=S)C1-6-alkyl, C(=O)aryl, C(=S)aryl, C(=O)C1-6-alkyl-aryl, C(=S)C1-6-alkyl-aryl, C(=O)-heteroaryl, C(=S)-heteroaryl, C(=O)-cycloalkyl, C(=S)-cycloalkyl, CO2H, CO2-alkyl, CO2-alkyl-aryl, C(=O)NH2, C(=O)NH-alkyl, C(=O)NH-aryl, C(=O)NH-cycloalkyl, C(=O)N(alkyl)2, C(=O)N(alkyl-aryl)2, C(=O)N(alkyl-heteroaryl)2, C(=O)N(cycloalkyl)2, S(O)-alkyl, S(O)-aryl, SO2-alkyl, SO2-aryl, SO2NH2, SO3H, CF3, =O, =S; —O—CH2-CH2-O—; alkyl, cycloalkyl, aryl and/or heteroaryl; on one atom or optionally on different atoms (it being possible for a substituent itself to be substituted). Polysubstitution is effected with the same substituent or with different substituents.

The term salt is understood as meaning any form of the active ingredient according to the invention in which the active ingredient assumes an ionic form or is charged and is coupled with a counter-ion (a cation or anion) or is in solution. The term is also understood as meaning complexes of the active ingredient with other molecules and ions, especially complexes complexed via ionic interactions. The term is understood as meaning in particular (and this is also a preferred embodiment of this invention) physiologically acceptable salts, in particular physiologically acceptable salts with cations or bases and physiologically acceptable salts with anions or acids or a salt formed with a physiologically acceptable acid or a physiologically acceptable cation.

The term of the physiologically acceptable salt with anions or acids is understood within the scope of this invention as meaning salts of at least one of the compounds according to the invention—in most cases protonated, for example at the nitrogen—as the cation with at least one anion, which are physiologically acceptable—especially when used in humans and/or mammals. In particular, the term is understood within the scope of this invention as meaning the salt formed with a physiologically acceptable acid, namely salts of the particular active ingredient with inorganic or organic acids, which are physiologically acceptable—especially when used in humans and/or mammals. Examples of physiologically acceptable salts of particular acids are salts of: hydrochloric acid, hydrobromic acid, sulfuric acid, methanesulfonic acid, formic acid, acetic acid, oxalic acid, succinic acid, malic acid, tartaric acid, mandelic acid, fumaric acid, lactic acid, citric acid, glutamic acid, saccharic acid, monomethylsebacic acid, 5-oxo-proline, hexane-1-sulfonic acid, nicotinic acid, 2-, 3- or 4-aminobenzoic acid, 2,4,6-trimethyl-benzoic acid, α-liponic acid, acetylglycine, phosphoric acid, maleic acid, malonic acid, hippuric acid and/or aspartic acid. The hydrochloride salt, the citrate and the hemicitrate are particularly preferred.

The term of the salt formed with a physiologically acceptable acid is understood within the scope of this invention as meaning salts of the particular active ingredient with inorganic or organic acids, which are physiologically acceptable—especially when used in humans and/or mammals. The hydrochloride and the citrate are particularly preferred. Examples of physiologically acceptable acids are: hydrochloric acid, hydrobromic acid, sulfuric acid, methanesulfonic acid, formic acid, acetic acid, oxalic acid, succinic acid, tartaric acid, mandelic acid, fumaric acid, lactic acid, citric acid, glutamic acid, saccharic acid, monomethylsebacic acid, 5-oxo-proline, hexane-1-sulfonic acid, nicotinic acid, 2-, 3- or 4-aminobenzoic acid, 2,4,6-trimethyl-benzoic acid, α-liponic acid, acetylglycine, hippuric acid and/or aspartic acid.

The term of the physiologically acceptable salt with cations or bases is understood within the scope of this invention as meaning salts of at least one of the compounds according to the invention—in most cases of a (deprotonated) acid—as the anion with at least one cation, preferably an inorganic cation, which are physiologically acceptable—especially when used in humans and/or mammals. Particular preference is given to the salts of the alkali metals and alkaline earth metals and also ammonium salts, but especially (mono-) or (di-)sodium, (mono-) or (di-)potassium, magnesium or calcium salts.

The term of the salt formed with a physiologically acceptable cation is understood within the scope of this invention as meaning salts of at least one of the particular compounds as the anion with at least one inorganic cation which is physiologically acceptable—especially when used in humans and/or mammals. Particular preference is given to the salts of the alkali metals and alkaline earth metals and also ammonium salts, but especially (mono-) or (di-)sodium, (mono-) or (di-)potassium, magnesium or calcium salts.

In a preferred embodiment of the substituted cyclohexyl-1,4-diamine derivatives according to the invention, $R^1$ and $R^2$, independently of one another, represent H; $C_{1-5}$-alkyl, saturated or unsaturated, branched or unbranched, mono- or poly-substituted or unsubstituted; or the radicals $R^1$ and $R^2$ together form a ring and denote $CH_2CH_2OCH_2CH_2$, $CH_2CH_2NR^{10}CH_2CH_2$ or $(CH_2)_{3-6}$, wherein $R^{10}$ represents H; $C^{1-8}$-alkyl, saturated or unsaturated, branched or unbranched, mono- or poly-substituted or unsubstituted.

Particular preference is given to substituted cyclohexyl-1,4-diamine derivatives in which $R^1$ and $R^2$, independently of one another, represent $CH_3$ or H, $R^1$ and $R^2$ not simultaneously representing H, or $R^1$ and $R^2$ represent $CH_2CH_2OCH_2CH_2$, $(CH_2)_4$, $(CH_2)_5$ or $(CH_2)_6$.

Preference is given also to substituted cyclohexyl-1,4-diamines in which $R^3$ represents cyclopentyl, cyclohexyl, phenyl, benzyl, naphthyl, anthracenyl, thiophenyl, benzothiophenyl, furyl, benzofuranyl, benzodioxolanyl, indolyl, indanyl, benzodioxanyl, pyrrolyl, pyridyl, pyrimidyl or pyrazinyl, in each case unsubstituted or mono- or poly-substituted; $C_{5-6}$-cycloalkyl, phenyl, naphthyl, anthracenyl, thiophenyl, benzothiophenyl, pyridyl, furyl, benzofuranyl, benzodioxolanyl, indolyl, indanyl, benzodioxanyl, pyrrolyl, pyrimidyl or pyrazinyl bonded via a saturated, unbranched $C_{1-2}$-alkyl group, in each case unsubstituted or mono- or poly-substituted;

in particular $R^3$ represents phenyl, furyl, thiophenyl, naphthyl, benzyl, benzofuranyl, indolyl, indanyl, benzodioxanyl, benzodioxolanyl, pyridyl, pyrimidyl, pyrazinyl or benzothiophenyl, in each case unsubstituted or mono- or poly-substituted; phenyl, furyl or thiophenyl bonded via a saturated, unbranched $C_{1-2}$-alkyl group, in each case unsubstituted or mono- or poly-substituted.

Particular preference is given to substituted cyclohexyl-1, 4-diamine derivatives in which $R^3$ represents phenyl, phenethyl, thiophenyl, pyridyl or benzyl, in each case substituted or unsubstituted, particularly preferably phenyl, pyridyl, thiophenyl, 4-chlorobenzyl, benzyl, 3-fluorophenyl, 3-chlorobenzyl, 4-methylbenzyl, 2-chlorobenzyl, 4-fluorobenzyl, 3-methylbenzyl, 2-methylbenzyl, 3-fluorobenzyl, 2-fluorobenzyl or phenethyl.

Preference is additionally given to substituted cyclohexyl-1,4-diamine derivatives in which B represents $(CR^5R^6)_n$.

Preference is further given to substituted cyclohexyl-1,4-diamine derivatives in which B represents aryl, heteroaryl or $C_{3-8}$-cycloalkyl, in each case mono- or poly-substituted or unsubstituted; or aryl bonded via $C_{1-3}$-alkyl (wherein an individual carbon atom of the alkyl chain may also be replaced by O), in each case mono- or poly-substituted or unsubstituted, wherein the $C_{1-3}$-alkyl chain may link the cyclic radical to A and/or N, that is to say two alkyl chains are optionally present.

Preference is given also to substituted cyclohexyl-1,4-diamine derivatives in which $R^5$ and $R^6$ represent H, $C_{1-5}$-alkyl, in each case saturated or unsaturated, branched or unbranched, mono- or poly-substituted or unsubstituted; aryl, in each case mono- or poly-substituted or unsubstituted; or aryl or $C_{3-8}$-cycloalkyl bonded via $C_{1-2}$-alkyl, in each case mono- or poly-substituted or unsubstituted.

Particular preference is given to cyclohexyl-1,4-diamine derivatives in which $R^5$ and $R^6$ represent H, $C_{1-5}$-alkyl, benzyl or phenyl.

Preference is given also to cyclohexyl-1,4-diamine derivatives in which $R^7$ represents H.

Preference is given also to cyclohexyl-1,4-diamine derivatives in which $R^8$ represents $C_{1-5}$-alkyl, cyclohexyl, cyclopentyl, cyclobutyl, cycloheptyl, cyclooctyl, phenyl, benzyl, naphthyl, thiophenyl, benzothiophenyl, furanyl, pyrazolyl, benzofuranyl, benzodioxolanyl, isoquinolinyl, indolyl, pyrrolyl, pyridyl, -pyrimidyl or pyrazinyl, in each case unsubstituted or mono- or poly-substituted; phenyl, naphthyl, thiophenyl, benzothiophenyl, pyridyl, furyl, benzofuranyl, indolyl, benzodioxanyl, pyrrolyl, pyrimidyl or pyrazinyl bonded via a saturated, unbranched substituted or unsubstituted $C_{1-2}$-alkyl group, in each case unsubstituted or mono- or poly-substituted, and $R^9$ represents $OR^{11}$, $C_{1-5}$-alkyl, cyclohexyl, cyclopentyl, cyclobutyl, cycloheptyl, cyclooctyl, phenyl, benzyl, naphthyl, thiophenyl, benzothiophenyl, furanyl, pyrazolyl, benzofuranyl, benzodioxolanyl, isoquinolinyl, indolyl, pyrrolyl, pyridyl, pyrimidyl or pyrazinyl, in each case unsubstituted or mono- or poly-substituted; phenyl, naphthyl, thiophenyl, benzothiophenyl, pyridyl, furyl, benzofuranyl, indolyl, benzodioxanyl, pyrrolyl, pyrimidyl or pyrazinyl bonded via a saturated, unbranched substituted or unsubstituted $C_{1-2}$-alkyl group, in each case unsubstituted or mono- or poly-substituted.

Particular preference is given to substituted cyclohexyl-1, 4-diamine derivatives in which $R^8$ represents phenyl, $C_{1-5}$-alkyl, branched or unbranched, saturated or unsaturated, or benzyl, in each case unsubstituted or mono- or poly-substituted, and $R^9$ represents $OR^{11}$, phenyl, $C_{1-5}$-alkyl, branched or unbranched, saturated or unsaturated, or benzyl, in each case unsubstituted or mono- or poly-substituted.

Preference is given also to substituted cyclohexyl-1,4-diamine derivatives in which $R^{11}$ represents $C_{1-5}$-alkyl, cyclohexyl, cyclopentyl, cycloheptyl, cyclooctyl, phenyl, benzyl, naphthyl, thiophenyl, benzothiophenyl, furanyl, pyrazolyl, benzofuranyl, indolyl, pyrrolyl, pyridyl, pyrimidyl or pyrazinyl, in each case unsubstituted or mono- or poly-substituted; phenyl, naphthyl, thiophenyl, benzothiophenyl, pyridyl, furyl, benzofuranyl, indolyl, pyrrolyl, pyrimidyl or pyrazinyl bonded via a saturated, unbranched substituted or unsubstituted $C_{1-2}$-alkyl group, in each case unsubstituted or mono- or poly-substituted.

Particular preference is given to substituted cyclohexyl-1, 4-diamine derivatives in which $R^{11}$ represents phenyl, $C_{1-5}$-alkyl, branched or unbranched, saturated or unsaturated, benzyl or methylfluorenyl, in each case unsubstituted or mono- or poly-substituted.

Very particular preference is given to substituted cyclohexyl-1,4-diamine derivatives from the group ({1-[4-dimethylamino-4-(3-fluoro-phenyl)-cyclohexylcarbamoyl]-3-methyl-butylcarbamoyl}-methyl)-carbamic acid benzyl ester {2-[4-dimethylamino-4-(3-fluoro-phenyl)-cyclohexylcarbamoyl]-ethyl}-carbamic acid tert.-butyl ester {[1-(4-dimethylamino-4-thiophen-2-yl-cyclohexylcarbamoyl) -3-methyl-butyl-carbamoyl]-methyl}-carbamic acid benzyl ester N-(4-dimethylamino-4-thiophen-2-yl-cyclohexyl)-3-phenyl-2-(tolyl-4-sulfonylamino)-propionamide

[1-(4-dimethylamino-4-thiophen-2-yl-cyclohexylcarbamoyl)-ethyl]-carbamic acid benzyl ester N-(4-dimethylamino-4-pyridin-2-yl-cyclohexyl)-3-phenyl-2-(tolyl-4-sulfonylamino) -propionamide {[1-(4-dimethylamino-4-phenyl-cyclohexylcarbamoyl)-3-methyl-butylcarbamoyl]-methyl}-carbamic acid benzyl ester {[4-dimethylamino-4-(2-methyl-benzyl)-cyclohexylcarbamoyl]-phenyl-methyl}-carbamic acid benzyl ester

[(4-azepan-1-yl-4-benzyl-cyclohexylcarbamoyl)-phenyl-methyl]-carbamic acid benzyl ester {[4-(2-chloro-benzyl)-4-dimethylamino-cyclohexylcarbamoyl]-phenyl-methyl}-carbamic acid benzyl ester {1-[4-(2-chloro-benzyl)-4-dimethylamino-cyclohexylcarbamoyl]-ethyl}-carbamic acid benzyl ester {[1-(4-benzyl-4-dimethylamino-cyclohexylcarbamoyl)-3-methyl-butylcarbamoyl]-methyl}-carbamic acid benzyl ester {1-[4-dimethylamino-4-(2-methyl-benzyl)-cyclohexylcarbamoyl]-2-phenyl-ethyl}-carbamic acid benzyl ester ({1-[4-dimethylamino-4-(2-fluoro-benzyl)-cyclohexylcarbamoyl]-3-methyl-butyl-carbamoyl}-methyl)-carbamic acid benzyl ester N-{1-[4-dimethylamino-4-(4-fluoro-benzyl)-cyclohexylcarbamoyl]-3-methyl-butyl}-benzamide {1-[4-(2-chloro-benzyl)-4-dimethylamino-cyclohexylcarbamoyl]-2-phenyl-ethyl}-carbamic acid tert.-butyl ester {1-[4-dimethylamino-4-(2-fluoro-benzyl)-cyclohexylcarbamoyl]-2-phenyl-ethyl}-carbamic acid tert.-butyl ester ({1-[4-dimethylamino-4-(3-methyl-benzyl)-cyclohexylcarbamoyl]-3-methyl-butyl-carbamoyl}-methyl)-carbamic acid benzyl ester ({1-[4-dimethylamino-4-(3-fluoro-benzyl)-cyclohexylcarbamoyl]-3-methyl-butyl-carbamoyl}-methyl)-carbamic acid benzyl ester
{[1-(4-dimethylamino-4-phenethyl-cyclohexylcarbamoyl)-3-methyl-butylcarbamoyl]-methyl}-carbamic acid benzyl ester
2-acetylamino-hexanoic acid [4-(2-chloro-benzyl)-4-dimethylamino-cyclohexyl]-amide
N-[4-(2-chloro-benzyl)-4-dimethylamino-cyclohexyl]-3-phenyl-2-(tolyl-4-sulfonyl-amino)-propionamide
3-tert.-butoxycarbonylamino-N-[4-(2-chloro-benzyl)-4-dimethylamino-cyclohexyl]-succinic acid cyclohexyl ester
{1-[4-dimethylamino-4-(3-methyl-benzyl)-cyclohexylcarbamoyl]-2-phenylethyl}-carbamic acid tert.-butyl ester
({1-[4-dimethylamino-4-(2-methyl-benzyl)-cyclohexylcarbamoyl]-3-methyl-butyl-carbamoyl}-methyl)-carbamic acid benzyl ester
{1-[4-dimethylamino-4-(2-methyl-benzyl)-cyclohexylcarbamoyl]-ethyl}-carbamic acid benzyl ester
{1-[4-dimethylamino-4-(2-methyl-benzyl)-cyclohexylcarbamoyl]-2-phenyl-ethyl}-carbamic acid tert.-butyl ester
({1-[4-(3-chloro-benzyl)-4-dimethylamino-cyclohexylcarbamoyl]-3-methyl-butyl-carbamoyl}-methyl)-carbamic acid benzyl ester
({1-[4-dimethylamino-4-(4-methyl-benzyl)-cyclohexylcarbamoyl]-3-methyl-butyl-carbamoyl}-methyl)-carbamic acid benzyl ester
[1-(4-dimethylamino-4-phenethyl-cyclohexylcarbamoyl)-ethyl]-carbamic acid benzyl ester
{1-[4-dimethylamino-4-(3-methyl-benzyl)-cyclohexylcarbamoyl]-2-hydroxy-ethyl}-carbamic acid tert.-butyl ester
[5-(4-benzyl-4-dimethylamino-cyclohexylcarbamoyl)-pentyl]-carbamic acid benzyl ester
{1-[4-(3-chloro-benzyl)-4-dimethylamino-cyclohexylcarbamoyl]-2-hydroxy-ethyl}-carbamic acid tert.-butyl ester
N-[4-dimethylamino-4-(2-methyl-benzyl)-cyclohexyl]-3-phenyl-2-(tolyl-4-sulfonyl-amino)-propionamide
4-chloro-N-[2-(4-{1-[4-dimethylamino-4-(2-methyl-benzyl)-cyclohexylcarbamoyl]-1-methyl-ethoxy}-phenyl)-ethyl]-benzamide
[1-(4-benzyl-4-dimethylamino-cyclohexylcarbamoyl)-2-phenyl-ethyl]-carbamic acid tert.-butyl ester
{1-[4-dimethylamino-4-(3-fluoro-benzyl)-cyclohexylcarbamoyl]-2-phenyl-ethyl}-carbamic acid tert.-butyl ester
({1-[4-(4-chloro-benzyl)-4-dimethylamino-cyclohexylcarbamoyl]-3-methyl-butyl-carbamoyl}-methyl)-carbamic acid benzyl ester
{1-[4-dimethylamino-4-(4-fluoro-benzyl)-cyclohexylcarbamoyl]-2-methyl-propyl}-carbamic acid 9H-fluoren-9-ylmethyl ester
{1-[4-dimethylamino-4-(3-methyl-benzyl)-cyclohexylcarbamoyl]-ethyl}-carbamic acid benzyl ester
{1-[4-dimethylamino-4-(2-methyl-benzyl)-cyclohexylcarbamoyl]-2-methyl-propyl}-carbamic acid 9H-fluoren-9-ylmethyl ester
{1-[4-(3-chloro-benzyl)-4-dimethylamino-cyclohexylcarbamoyl]-ethyl}-carbamic acid benzyl ester
{[1-(4-benzyl-4-piperidin-1-yl-cyclohexylcarbamoyl)-3-methyl-butylcarbamoyl]-methyl}-carbamic acid benzyl ester
{5-[4-dimethylamino-4-(4-methyl-benzyl)-cyclohexylcarbamoyl]-pentyl}-carbamic acid benzyl ester
{[3-methyl-1-(4-phenyl-4-piperidin-1-yl-cyclohexylcarbamoyl) -butylcarbamoyl]-methyl}-carbamic acid benzyl ester
{1-[4-dimethylamino-4-(4-methyl-benzyl)-cyclohexylcarbamoyl]-2-hydroxy-ethyl}-carbamic acid tert.-butyl ester
[1-(4-benzyl-4-dimethylamino-cyclohexylcarbamoyl)-ethyl}-carbamic acid benzyl ester
{1-[4-dimethylamino-4-(4-methyl-benzyl)-cyclohexylcarbamoyl)-ethyl}-carbamic acid benzyl ester
[1-(4-benzyl-4-piperidin-1-yl-cyclohexylcarbamoyl)-3-carbamoyl-propyl]-carbamic acid tert.-butyl ester
2-acetylamino-pent-4-enoic acid [4-(2-chloro-benzyl)-4-dimethylamino-cyclohexyl]-amide
[2-hydroxy-1-(4-phenyl-4-piperidin-1-yl-cyclohexylcarbamoyl)-ethyl]-carbamic acid tert.-butyl ester
4-chloro-N-[2-(4-{1-[4-(2-chloro-benzyl)-4-dimethylamino-cyclohexylcarbamoyl]-1-methyl-ethoxy}-phenyl)-ethyl]-benzamide
{3-carbamoyl-1-[4-(4-chloro-benzyl)-4-dimethylamino-cyclohexylcarbamoyl]-propyl}-carbamic acid tert.-butyl ester
[1-(4-benzyl-4-piperidin-1-yl-cyclohexylcarbamoyl)-ethyl]-carbamic acid benzyl ester
[2-(4-dimethylamino-4-phenethyl-cyclohexylcarbamoyl)-ethyl]-carbamic acid tert.-butyl ester
{1-[4-(4-chloro-benzyl)-4-dimethylamino-cyclohexylcarbamoyl]-ethyl}-carbamic acid benzyl ester
{1-[4-dimethylamino-4-(4-methyl-benzyl)-cyclohexylcarbamoyl]-2-phenyl-ethyl}-carbamic acid tert.-butyl ester
[1-(4-morpholin-4-yl-4-phenyl-cyclohexylcarbamoyl)-2-phenyl-ethyl]-carbamic acid tert.-butyl ester
{1-[4-dimethylamino-4-(3-fluoro-benzyl)-cyclohexylcarbamoyl]-ethyl}-carbamic acid benzyl ester
{2-[4-(4-chloro-benzyl)-4-dimethylamino-cyclohexylcarbamoyl]-ethyl}-carbamic acid tert.-butyl ester
[2-hydroxy-1-(4-morpholin-4-yl-4-phenyl-cyclohexylcarbamoyl)-ethyl]-carbamic acid tert.-butyl ester
{1-[4-(4-chloro-benzyl)-4-dimethylamino-cyclohexylcarbamoyl]-2-hydroxy-ethyl}-carbamic acid tert.-butyl ester
{2-[4-dimethylamino-4-(4-methyl-benzyl)-cyclohexylcarbamoyl]-ethyl}-carbamic acid tert.-butyl ester
{1-[4-(4-chloro-benzyl)-4-dimethylamino-cyclohexylcarbamoyl]-2-phenyl-ethyl}-carbamic acid tert.-butyl ester
[1-(4-azepan-1-yl-4-benzyl-cyclohexylcarbamoyl)-2-phenyl-ethyl]-carbamic acid tert.-butyl ester
{2-[4-dimethylamino-4-(3-fluoro-benzyl)-cyclohexylcarbamoyl]-ethyl}-carbamic acid tert.-butyl ester
[1-(4-morpholin-4-yl-4-phenyl-cyclohexylcarbamoyl)-ethyl]-carbamic acid benzyl ester
[1-(4-benzyl-4-piperidin-1-yl-cyclohexylcarbamoyl)-2-hydroxy-ethyl]-carbamic acid tert.-butyl ester
2-(2,2,2-trifluoro-acetyl)-1,2,3,4-tetrahydro-isoquinoline-7-sulfonic acid (4-benzyl-4-pyrrolidin-1-yl-cyclohexyl)-amide
[2-phenyl-1-(4-phenyl-4-piperidin-1-yl-cyclohexylcarbamoyl)-ethyl]-carbamic acid tert.-butyl ester
{[3-methyl-1-(4-morpholin-4-yl-4-phenyl-cyclohexylcarbamoyl) -butylcarbamoyl]-methyl}-carbamic acid benzyl ester in the form of the racemate; in the form of the enantiomers, diastereoisomers, mixtures of the enantiomers or diastereoisomers or in the form of an individual enantiomer or diastereoisomer; in the form of the bases and/or salts of physiologically acceptable acids or cations.

The substances according to the invention act, for example, on the µ-opioid receptor, which is relevant in connection with various diseases, so that they are suitable as a pharmaceutical active ingredient in a medicament. The invention therefore also provides medicaments comprising at least one substituted cyclohexylcarboxylic acid derivative according to the invention and also, optionally, suitable additives and/or auxiliary substances and/or, optionally, further active ingredients.

In addition to at least one substituted cyclohexyl-1,4-diamine derivative according to the invention, the medicaments according to the invention optionally comprise suitable additives and/or auxiliary substances, that is to say also carriers, fillers, solvents, diluents, colourings and/or binders, and can be administered as liquid medicament forms in the form of injection solutions, drops or juices, as semi-solid medicament forms in the form of granules, tablets, pellets, patches, capsules, plasters/spray-on plasters or aerosols. The choice of the auxiliary substances etc. and the amounts thereof to be employed depend on whether the medicament is to be administered orally, perorally, parenterally, intravenously, intraperitoneally, intradermally, intramuscularly, intranasally, buccally, rectally or locally, for example to the skin, the mucous membranes or in the eyes. Formulations in the form of tablets, dragées, capsules, granules, drops, juices and syrups are suitable for oral administration; solutions, suspensions, readily reconstitutable dry formulations and sprays are suitable for parenteral and topical administration and for administration by inhalation. Substituted cyclohexyl-1,4-diamine derivatives according to the invention in a depot, in dissolved form or in a plaster, optionally with the addition of agents which promote penetration through the skin, are suitable formulations for percutaneous administration. Preparation forms which can be used orally or percutaneously can release the substituted cyclohexyl-1,4-diamine derivatives according to the invention in a delayed manner. The substituted cyclohexyl-1,4-diamine derivatives according to the invention can also be administered in parenteral long-term depot forms, such as, for example, implants or implanted pumps. Other further active ingredients known to the person skilled in the art can in principle be added to the medicaments according to the invention.

The amount of active ingredient to be administered to the patients varies in dependence on the weight of the patient, the mode of administration, the indication and the severity of the disease. From 0.00005 to 50 mg/kg, preferably from 0.01 to 5 mg/kg, of at least one substituted cyclohexyl-1,4-diamine derivative according to the invention are conventionally administered.

For all the above forms of the medicaments according to the invention it is particularly preferred for the medicament to comprise, in addition to at least one substituted cyclohexyl-1,4-diamine derivative, also a further active ingredient, in particular an opioid, preferably a strong opioid, especially morphine, or an anaesthetic, preferably hexobarbital or halothane.

In a preferred form of the medicament, a substituted cyclohexyl-1,4-diamine derivative according to the invention that is present is in the form of the pure diastereoisomer and/or enantiomer, in the form of the racemate or in the form of a non-equimolar or equimolar mixture of the diastereoisomers and/or enantiomers.

The ORL1 receptor, and also the other opioid receptors, have been identified especially in the occurrence of pain. Accordingly, substituted cyclohexyl-1,4-diamine derivatives according to the invention can be used in the preparation of a medicament for the treatment of pain, in particular of acute, neuropathic or chronic pain.

The invention therefore relates also to the use of a substituted cyclohexyl-1,4-diamine derivative according to the invention in the preparation of a medicament for the treatment of pain, in particular of acute, visceral, neuropathic or chronic pain.

The invention relates further to the use of a substituted cyclohexyl-1,4-diamine derivative according to the invention in the preparation of a medicament for the treatment of anxiety, stress and syndromes associated with stress, depression, epilepsy, Alzheimer's disease, senile dementia, catalepsy, general cognitive dysfunctions, learning and memory disorders (as a nootropic agent), withdrawal symptoms, alcohol and/or drug and/or medicament abuse and/or dependency, sexual dysfunctions, cardiovascular diseases, hypotension, hypertension, tinnitus, pruritus, migraine, impaired hearing, deficient intestinal motility, impaired food intake, anorexia, obesity, locomotor disorders, diarrhoea, cachexia, urinary incontinence or as a muscle relaxant, anticonvulsive or anaesthetic or for co-administration on treatment with an opioid analgesic or with an anaesthetic, for diuresis or antinatriuresis, anxiolysis, for modulating motor activity, for modulating neurotransmitter secretion and treatment of neurodegenerative diseases associated therewith, for the treatment of withdrawal symptoms and/or for reducing the addictive potential of opoids.

It may be preferable in one of the above uses for a substituted cyclohexyl-1,4-diamine derivative that is used to be present in the form of the pure diastereoisomer and/or enantiomer, in the form of the racemate or in the form of a non-equimolar or equimolar mixture of the diastereoisomers and/or enantiomers.

The invention further provides a method of treating, especially in one of the above-mentioned indications, a non-human mammal or a human requiring the treatment of pain, especially chronic pain, by administration of a therapeutically effective dose of a substituted cyclohexyl-1,4-diamine derivative according to the invention or of a medicament according to the invention.

The invention further provides a process for the preparation of the substituted cyclohexyl-1,4-diamine derivatives according to the invention as described in the following description and examples.

The radicals $R^{01}$ and $R^{02}$ have the meanings given for $R^1$ and $R^2$ for compounds of formula I according to the invention and may additionally, independently of one another, represent a protecting group. The remaining radicals have the meanings given for formula I:

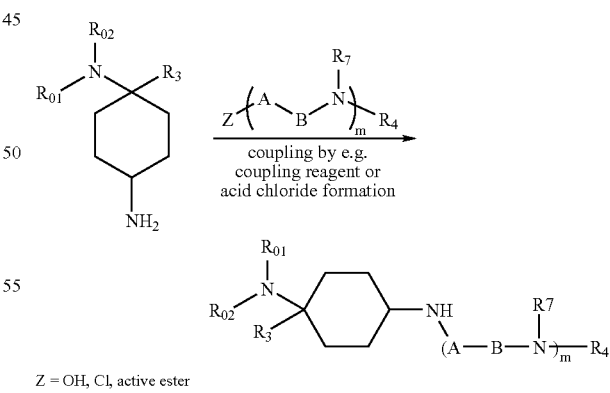

The various methods known to the person skilled in the art for the preparation of amides are in principle suitable for the preparation of the substances according to the invention.

The process according to the invention is preferably based on linking substituted cyclohexane-1,4-diamines (WO 02090317) to suitable carboxylic or sulfonic acids and/or carboxylic or sulfonic acid derivatives, especially acid chlorides or bromides, and thus converting them into compounds according to the invention. In reactions with acid chlorides and bromides, polar or non-polar aprotic solvents are used, to which there has been added an organic or inorganic auxiliary base, preferably tertiary amines such as triethylamine, diisopropylethylamine or DMAP. In addition to such amines, pyridine, for example, is also suitable as the base and as the solvent. Preferably, acid chlorides are reacted with amines at from −30 to +40° C. in dichloromethane or chloroform in the presence of triethylamine or pyridine and, optionally, catalytic amounts of DMAP. For the reaction of carboxylic acids with a substituted cyclohexane-1,4-diamine (WO 0209317), the entire range of methods known to the person skilled in the art for the preparation of amides is available. It is advantageous in this case to use organic or inorganic water-removing agents, such as, for example, molecular sieve, magnesium sulfate, sulfuric acid or carbodiimides such as DCC or DIC, the latter optionally in the presence of HOBt. These reactions are also preferably carried out in polar or non-polar aprotic solvents at temperatures of from −30 to +110° C., preferably from −10 to +40° C. The protecting groups are optionally subsequently removed.

EXAMPLES

Certain embodiments of the present invention may be further understood by reference to the following specific examples. These examples and the terminology used herein are for the purpose of describing particular embodiments only and are not intended to be limiting.

The yields of the compounds prepared have not been optimised.

All temperatures are uncorrected.

The term "ether" means diethyl ether, "EE" means ethyl acetate and "DCM" means dichloromethane. The term "equivalents" means substance amount equivalents, "m.p." means melting point or melting range, "decomp." means decomposition, "RT" means room temperature, "abs." means absolute (anhydrous), "rac." means racemic, "conc." means concentrated, "min." means minutes, "h" means hours, "d" means days, "vol. %" means percent by volume, "wt. %" means percent by weight and "M" is the concentration stated in mol./l.

Silica gel 60 (0.040-0.063 mm) from E. Merck, Darmstadt, was employed as the stationary phase for the column chromatography.

The thin-layer chromatography analyses were carried out with HPTLC pre-coated plates, silica gel 60 F 254 from E. Merck, Darmstadt.

The mixing ratios of mobile phases for chromatography analyses are always stated in volume/volume.

The compounds used in the following were either commercially available or their preparation is known from the prior art or has been derived from the prior art in a manner obvious to the person skilled in the art.

General procedure:

To 0.1 mmol. of the cyclohexane-1,4-diamine there was added 0.1 mmol. of an acid chloride prepared from the appropriate carboxylic acids or sulfonic acids according to methods known to the person skilled in the art (see Table 1), in the presence of 1.05 equivalents of triethylamine. Stirring was carried out for 12 h, and a 1M sodium carbonate solution was then added. Extraction with 3×2 ml of dichloromethane and removal of the solvent yielded the product.

In Table 1, the acids used for the last step for the examples are indicated.

TABLE 1

Names of the exemplary compounds and carboxylic acids used in the last synthesis step.

| Compound | Acid used | Name |
|---|---|---|
| Example 1 | | ({1-[4-Dimethylamino-4-(3-fluorophenyl)-cyclohexylcarbamoyl]-3-methyl-butylcarbamoyl}-methyl)-carbamic acid benzyl ester |
| Example 2 | | {2-[4-Dimethylamino-4-(3-fluorophenyl)-cyclohexylcarbamoyl]-ethyl}-carbamic acid tert.-butyl ester |
| Example 3 | | {[1-(4-Dimethylamino-4-thiophen-2-yl-cyclohexylcarbamoyl)-3-methyl-butylcarbamoyl]-methyl}-carbamic acid benzyl ester |

TABLE 1-continued

Names of the exemplary compounds and carboxylic acids used in the last synthesis step.

| Compound | Acid used | Name |
| --- | --- | --- |
| Example 4 | (structure) | N-(4-Dimethylamino-4-thiophen-2-yl-cyclohexyl)-3-phenyl-2-(tolyl-4-sulfonylamino)-propionamide |
| Example 5 | (structure) | [1-(4-Dimethylamino-4-thiophen-2-yl-cyclohexylcarbamoyl)-ethyl]-carbamic acid benzyl ester |
| Example 6 | (structure) | N-(4-Dimethylamino-4-pyridin-2-yl-cyclohexyl)-3-phenyl-2-(tolyl-4-sulfonylamino)-propionamide |
| Example 7 | (structure) | {[1-(4-Dimethylamino-4-phenyl-cyclohexylcarbamoyl)-3-methyl-butylcarbamoyl]-methyl}-carbamic acid benzyl ester |
| Example 8 | (structure) | {[4-Dimethylamino-4-(2-methyl-benzyl)-cyclohexylcarbamoyl]-phenyl-methyl}-carbamic acid benzyl ester |
| Example 9 | (structure) | [(4-Azepan-1-yl-4-benzyl-cyclohexylcarbamoyl)-phenyl-methyl]-carbamic acid benzyl ester |

TABLE 1-continued

Names of the exemplary compounds and carboxylic acids used in the last synthesis step.

| Compound | Acid used | Name |
| --- | --- | --- |
| Example 10 | (structure) | {[4-(2-Chloro-benzyl)-4-dimethylamino-cyclohexylcarbamoyl]-phenyl-methyl}-carbamic acid benzyl ester |
| Example 11 | (structure) | {1-[4-(2-Chloro-benzyl)-4-dimethylamino-cyclohexylcarbamoyl]-ethyl}-carbamic acid benzyl ester |
| Example 12 | (structure) | {[1-(4-Benzyl-4-dimethylamino-cyclohexylcarbamoyl)-3-methyl-butylcarbamoyl]-methyl}-carbamic acid benzyl ester |
| Example 13 | (structure) | {1-[4-Dimethylamino-4-(2-methyl-benzyl)-cyclohexylcarbamoyl]-2-phenyl-ethyl}-carbamic acid benzyl ester |
| Example 14 | (structure) | ({1-[4-Dimethylamino-4-(2-fluoro-benzyl)-cyclohexylcarbamoyl]-3-methyl-butylcarbamoyl}-methyl)-carbamic acid benzyl ester |
| Example 15 | (structure) | N-{1-[4-Dimethylamino-4-(4-fluoro-benzyl)-cyclohexylcarbamoyl]-3-methyl-butyl}-benzamide |

TABLE 1-continued

Names of the exemplary compounds and carboxylic acids used in the last synthesis step.

| Compound | Acid used | Name |
| --- | --- | --- |
| Example 16 | (structure) | {1-[4-(2-Chloro-benzyl)-4-dimethylamino-cyclohexylcarbamoyl]-2-phenyl-ethyl}-carbamic acid tert.-butyl ester |
| Example 17 | (structure) | {1-[4-Dimethylamino-4-(2-fluoro-benzyl)-cyclohexylcarbamoyl]-2-phenyl-ethyl}-carbamic acid tert.-butyl ester |
| Example 18 | (structure) | ({1-[4-Dimethylamino-4-(3-methyl-benzyl)-cyclohexylcarbamoyl]-3-methyl-butylcarbamoyl}-methyl)-carbamic acid benzyl ester |
| Example 19 | (structure) | ({1-[4-Dimethylamino-4-(3-fluoro-benzyl)-cyclohexylcarbamoyl]-3-methyl-butylcarbamoyl}-methyl)-carbamic acid benzyl ester |
| Example 20 | (structure) | {[1-(4-Dimethylamino-4-phenethyl-cyclohexylcarbamoyl)-3-methyl-butylcarbamoyl]-methyl}-carbamic acid benzyl ester |
| Example 21 | (structure) | 2-Acetylamino-hexanoic acid [4-(2-chloro-benzyl)-4-dimethylamino-cyclohexyl]-amide |
| Example 22 | (structure) | N-[4-(2-Chloro-benzyl)-4-dimethylamino-cyclohexyl]-3-phenyl-2-(tolyl-4-sulfonylamino)-propionamide |

TABLE 1-continued

Names of the exemplary compounds and carboxylic acids used in the last synthesis step.

| Compound | Acid used | Name |
| --- | --- | --- |
| Example 23 | | 3-tert.-Butoxycarbonylamino-N-[4-(2-chloro-benzyl)-4-dimethylamino-cyclohexyl]-sucinic acid cyclohexyl ester |
| Example 24 | | {1-[4-Dimethylamino-4-(3-methyl-benzyl)-cyclohexylcarbamoyl]-2-phenyl-ethyl}-carbamic acid tert.-butyl ester |
| Example 25 | | ({1-[4-Dimethylamino-4-(2-methyl-benzyl)-cyclohexylcarbamoyl]-3-methyl-butylcarbamoyl}-methyl)-carbamic acid benzyl ester |
| Example 26 | | {1-[4-Dimethylamino-4-(2-methyl-benzyl)-cyclohexylcarbamoyl]-ethyl}-carbamic acid benzyl ester |
| Example 27 | | {1-[4-Dimethylamino-4-(2-methyl-benzyl)-cyclohexylcarbamoyl]-2-phenyl-ethyl}-carbamic acid tert.-butyl ester |
| Example 28 | | ({1-[4-(3-Chloro-benzyl)-4-dimethylamino-cyclohexylcarbamoyl]-3-methyl-butylcarbamoyl}-methyl)-carbamic acid benzyl ester |

TABLE 1-continued

Names of the exemplary compounds and carboxylic acids used in the last synthesis step.

| Compound | Acid used | Name |
| --- | --- | --- |
| Example 29 | | ({1-[4-Dimethylamino-4-(4-methyl-benzyl)-cyclohexylcarbamoyl]-3-methyl-butylcarbamoyl}-methyl)-carbamic acid benzyl ester |
| Example 30 | | [1-(4-Dimethylamino-4-phenethyl-cyclohexylcarbamoyl)-ethyl]-carbamic acid benzyl ester |
| Example 31 | | {1-[4-Dimethylamino-4-(3-methyl-benzyl)-cyclohexylcarbamoyl]-2-hydroxy-ethyl}-carbamic acid tert.-butyl ester |
| Example 32 | | [5-(4-Benzyl-4-dimethylamino-cyclohexylcarbamoyl)-pentyl]-carbamic acid benzyl ester |
| Example 33 | | {1-[4-(3-Chloro-benzyl)-4-dimethylamino-cyclohexylcarbamoyl]-2-hydroxy-ethyl}-carbamic acid tert.-butyl ester |
| Example 34 | | N-[4-Dimethylammino-4-(2-methyl-benzyl)-cyclohexyl]-3-phenyl-2-(tolyl-4-sulfonylamino)-propionamide |
| Example 35 | | 4-Chloro-N-[2-(4-{1-[4-dimethylamino-4-(2-methyl-benzyl)-cyclohexylcarbamoyl]-1-methyl-ethoxy}-phenyl)-ethyl]-benzamide |

TABLE 1-continued

Names of the exemplary compounds and carboxylic acids used in the last synthesis step.

| Compound | Acid used | Name |
| --- | --- | --- |
| Example 36 | | [1-(4-Benzyl-4-dimethylamino-cyclohexylcarbamoyl)-2-phenyl-ethyl]-carbamic acid tert.-butyl ester |
| Example 37 | | {1-(4-Dimethylamino-4-(3-fluoro-benzyl)-cyclohexylcarbamoyl]-2-phenyl-ethyl}-carbamic acid tert.-butyl ester |
| Example 38 | | ({1-[4-(4-Chloro-benzyl)-4-dimethylamino-cyclohexylcarbamoyl]-3-methyl-butylcarbamoyl}-methyl)-carbamic acid benzyl ester |
| Example 39 | | {1-[4-Dimethylamino-4-(4-fluoro-benzyl)-cyclohexylcarbamoyl]-2-methyl-propyl}-carbamic acid 9H-fluoren-9-ylmethyl ester |
| Example 40 | | {1-[4-Dimethylamino-4-(3-methyl-benzyl)-cyclohexylcarbamoyl]-ethyl}-carbamic acid benzyl ester |
| Example 41 | | {1-[4-Dimethylamino-4-(2-methyl-benzyl)-cyclohexylcarbamoyl]-2-methyl-propyl}-carbamic acid 9H-fluoren-9-ylmethyl ester |
| Example 42 | | {1-[4-(3-Chloro-benzyl)-4-dimethylamino-cyclohexylcarbamoyl]-ethyl}-carbamic acid benzyl ester |

TABLE 1-continued

Names of the exemplary compounds and carboxylic acids used in the last synthesis step.

| Compound | Acid used | Name |
|---|---|---|
| Example 43 | (structure) | {[1-(4-Benzyl-4-piperidin-1-yl-cyclohexylcarbamoyl)-3-methyl-butylcarbamoyl]-methyl}-carbamic acid benzyl ester |
| Example 44 | (structure) | {5-[4-Dimethylamino-4-(4-methyl-benzyl)-cyclohexylcarbamoyl]-pentyl}-carbamic acid benzyl ester |
| Example 45 | (structure) | {[3-Methyl-1-(4-phenyl-4-piperidin-1-yl-cyclohexylcarbamoyl)-butylcarbamoyl]-methyl}-carbamic acid benzyl ester |
| Example 46 | (structure) | {1-[4-Dimethylamino-4-(4-methyl-benzyl)-cyclohexylcarbamoyl]-2-hydroxy-ethyl}-carbamic acid tert.-butyl ester |
| Example 47 | (structure) | [1-(4-Benzyl-4-dimethylamino-cyclohexylcarbamoyl)-ethyl]-carbamic acid benzyl ester |
| Example 48 | (structure) | {1-[4-Dimethylamino-4-(4-methyl-benzyl)-cyclohexylcarbamoyl]-ethyl}-carbamic acid benzyl ester |
| Example 49 | (structure) | [1-(4-Benzyl-4-piperidin-1-yl-cyclohexylcarbamoyl)-3-carbamoyl-propyl]-carbamic acid tert.-butyl ester |

TABLE 1-continued

Names of the exemplary compounds and carboxylic acids used in the last synthesis step.

| Compound | Acid used | Name |
| --- | --- | --- |
| Example 50 | 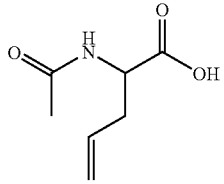 | 2-Acetylamino-pent-4-enoic acid [4-(2-chloro-benzyl)-4-dimethylamino-cyclohexyl]-amide |
| Example 51 | 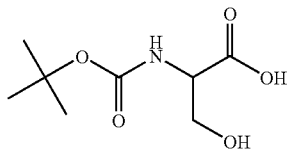 | [2-Hydroxy-1-(4-phenyl-4-piperidin-1-yl-cyclohexylcarbamoyl)-ethyl]-carbamic acid tert.-butyl ester |
| Example 52 | 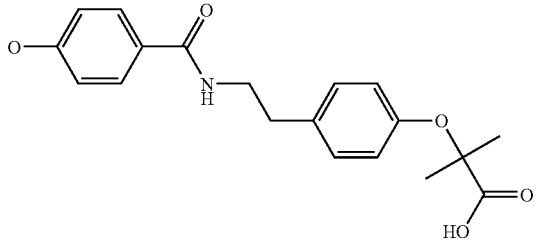 | 4-Chloro-N-[2-(4-{1-[4-(2-chloro-benzyl)-4-dimethylamino-cyclohexylcarbamoyl]-1-methyl-ethoxy}-phenyl)-ethyl]-benzamide |
| Example 53 | 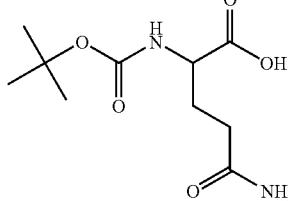 | {3-Carbamoyl-1-[4-(4-chloro-benzyl)-4-dimethylamino-cyclohexylcarbamoyl]-propyl}-carbamic acid tert.-butyl ester |
| Example 54 | 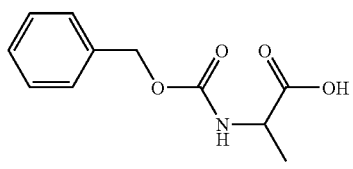 | [1-(4-Benzyl-4-piperidin-1-yl-cyclohexylcarbamoyl)-ethyl]-carbamic acid benzyl ester |
| Example 55 | 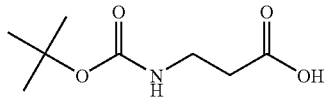 | [2-(4-Dimethylamino-4-phenethyl-cyclohexylcarbamoyl)-ethyl]-carbamic acid tert.-butyl ester |
| Example 56 | 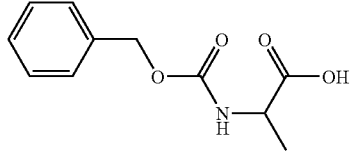 | {1-[4-(4-Chloro-benzyl)-4-dimethylamino-cyclohexylcarbamoyl]-ethyl}-carbamic acid benzyl ester |
| Example 57 | 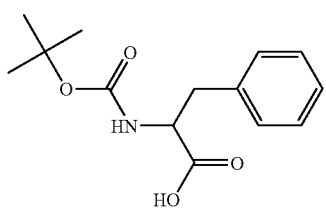 | {1-[4-Dimethylamino-4-(4-methyl-benzyl)-cyclohexylcarbamoyl]-2-phenyl-ethyl}-carbamic acid tert.-butyl ester |

TABLE 1-continued

Names of the exemplary compounds and carboxylic acids used in the last synthesis step.

| Compound | Acid used | Name |
|---|---|---|
| Example 58 | 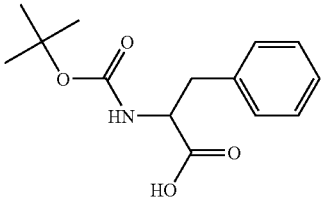 | [1-(4-Morpholin-4-yl-4-phenyl-cyclohexylcarbamoyl)-2-phenyl-ethyl]-carbamic acid tert.-butyl ester |
| Example 59 | 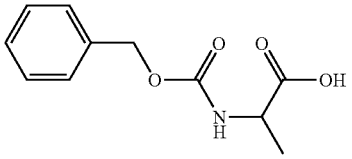 | {1-[4-Dimethylamino-4-(3-fluoro-benzyl)-cyclohexylcarbamoyl]-ethyl}-carbamic acid benzyl ester |
| Example 60 | 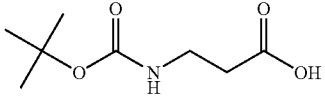 | {2-[4-(4-Chloro-benzyl)-4-dimethylamino-cyclohexylcarbamoyl]-ethyl}-carbamic acid tert.-butyl ester |
| Example 61 | 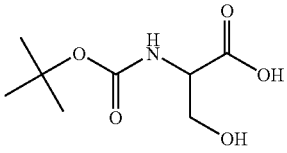 | [2-Hydroxy-1-(4-morpholin-4-yl-4-phenyl-cyclohexylcarbamoyl)-ethyl]-carbamic acid tert.-butyl ester |
| Example 62 | 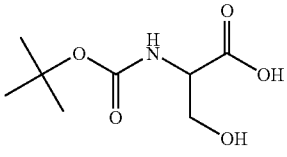 | {1-[4-(4-Chloro-benzyl-4-dimethylamino-cyclohexylcarbamoyl]-2-hydroxy-ethyl}-carbamic acid tert.-butyl ester |
| Example 63 | 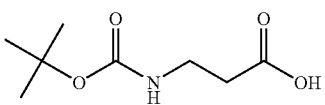 | {2-[4-Dimethylamino-4-(4-methyl-benzyl)-cyclohexylcarbamoyl]-ethyl}-carbamic acid tert.-butyl ester |
| Example 64 | 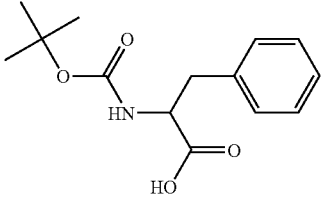 | {1-[4-(4-Chloro-benzyl)-4-dimethylamino-cyclohexylcarbamoyl]-2-phenyl-ethyl}-carbamic acid tert.-butyl ester |
| Example 65 | 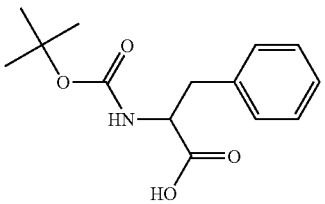 | [1-(4-Azepan-1-yl-4-benzyl-cyclohexylcarbamoyl)-2-phenyl-ethyl]-carbamic acid tert.-butyl ester |
| Example 66 | 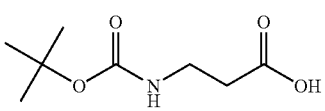 | {2-[4-Dimethylamino-4-(3-fluoro-benzyl)-cyclohexylcarbamoyl]-ethyl}-carbamic acid tert.-butyl ester |

TABLE 1-continued

Names of the exemplary compounds and carboxylic acids used in the last synthesis step.

| Compound | Acid used | Name |
|---|---|---|
| Example 67 | | [1-(4-Morpholin-4-yl-4-phenyl-cyclohexylcarbamoyl)-ethyl]-carbamic acid benzyl ester |
| Example 68 | | [1-(4-Benzyl-4-piperidin-1-yl-cyclohexylcarbamoyl)-2-hydroxy-ethyl]-carbamic acid tert.-butyl ester |
| Example 69 | | 2-(2,2,2-Trifluoro-acetyl)-1,2,3,4-tetrahydro-isoquinoline-7-sulfonic acid (4-benzyl-4-pyrolidin-1-yl-cyclohexyl)-amide |
| Example 70 | | [2-Phenyl-1-(4-phenyl-4-piperidin-1-yl-cyclohexylcarbamoyl)-ethyl]-carbamic acid tert.-butyl ester |
| Example 71 | | {[3-Methyl-1-(4-morpholin-4-yl-4-phenyl-cyclohexylcarbamoyl)-butylcarbamoyl]-methyl}-carbamic acid benzyl ester |

Tests of the Effectiveness of the Compounds According to the Invention:

Measurement of ORL1 Binding

The cyclohexane derivatives of the general formula I were investigated in a receptor binding assay with $^3$H-nociceptin/orphanin FQ with membranes of recombinant CHO-ORL1 cells. This test system was conducted in accordance with the method described by Ardati et al. (Mol. Pharmacol., 51, 1997, p. 816-824). The concentration of $^3$H-nociceptin/orphanin FQ in these experiments was 0.5 nM. The binding assays were carried out with in each case 20 μg membrane protein per 200 μl batch in 50 mM Hepes, pH 7.4, 10 mM MgCl$_2$ and 1 mM EDTA. The binding to the ORL1 receptor was determined using in each case 1 mg of WGA-SPA beads (Amersham-Pharmacia, Freiburg), by incubation of the batch for one hour at RT and subsequent measurement in a Trilux scintillation counter (Wallac, Finland). The affinity is given in Table 1 as the nanomolar $K_i$ value or % inhibition at c=1 μM.

Measurement of μBinding

The receptor affinity for the human μ-opiate receptor was determined in a homogeneous batch on microtitre plates. To that end, serial dilutions of the particular substituted cyclohexyl-1,4-diamine derivative to be tested were incubated for 90 minutes at room temperature with a receptor membrane preparation (15-40 μg of protein per 250 μl of incubation batch) of CHO-K1 cells, which express the human μ-opiate receptor (RB-HOM receptor membrane preparation from NEN, Zaventem, Belgium), in the presence of 1 nmol./l of the radioactive ligand [$^3$H]-naloxone (NET719, NEN, Zaventem, Belgium) and 1 mg of WGA-SPA beads (wheatgerm agglutinin SPA beads from Amersham/Pharmacia, Freiburg, Germany) in a total volume of 250 μl. The incubation buffer used was 50 mmol./l of Tris-HCl supplemented with 0.05 wt. % sodium azide and with 0.06 wt. % bovine serum albumin. In order to determine non-specific binding, 25 μmol./l of naloxone were additionally added. When the ninety-minute incubation time was complete, the microtitre plates were centrifuged off for 20 minutes at 1000 g and the radioactivity was measured in a β-counter (Microbeta-Trilux, PerkinElmer Wallac, Freiburg, Germany). The percentage displacement of the radioactive ligand from its binding to the human μ-Opiate receptor at a concentration of the test substances of 1 μmol./l was determined and stated as the percentage inhibition (% inhibition) of specific binding. In some cases, starting from the percentage displacement, $IC_{50}$ inhibitory concentrations, which effect 50% displacement of the radioactive ligand, were calculated by means of different concentrations of the compounds of the general formula I to be tested. Ki values for the test substances were obtained by conversion by means of the Cheng-Prusoff equation.

Measurement of Serotonin Reuptake

In order to be able to carry out these in vitro studies, synaptosomes were freshly isolated from areas of rat brain. A so-called "P2" fraction is used in each case, which is prepared according to the procedure of Gray and Whittaker (E. G. Gray and V. P. Whittaker (1962) J. Anat. 76, 79-88). For the 5HT uptake, these vesicular particles are isolated from the medulla + pons region of male rat brains.

A detailed description of the method can be found in the literature (M. Ch. Frink, H.-H. Hennies, W. Englberger, M. Haurand and B. Wilffert (1996) Arzneim.-Forsch./Drug Res. 46 (III), 11, 1029-1036).

Measurement of Noradrenaline Reuptake

In order to be able to carry out these in vitro studies, synaptosomes were freshly isolated from areas of rat brain. A so-called "$P_2$" fraction is used in each case, which is prepared according to the procedure of Gray and Whittaker (E. G. Gray and V. P. Whittaker (1962) J. Anat. 76, 79-88). For the NA uptake, these vesicular particles are isolated from the hypothalamus of male rat brains.

A detailed description of the method can be found in the literature (M. Ch. Frink, H.-H. Hennies, W. Englberger, M. Haurand and B. Wilffert (1996) Arzneim.-Forsch./Drug Res. 46 (III), 11, 1029-1036).

By way of example, the following binding data were determined:

| Compound | µ-Opiate receptor [1 µM], % inhibition |
|---|---|
| Example 1 | 101 |
| Example 2 | 97 |
| Example 3 | 97 |
| Example 4 | 96 |
| Example 5 | 96 |
| Example 6 | 95 |
| Example 7 | 95 |
| Example 8 | 86 |
| Example 9 | 84 |
| Example 10 | 82 |
| Example 11 | 82 |
| Example 12 | 79 |
| Example 13 | 78 |
| Example 14 | 78 |
| Example 15 | 76 |
| Example 16 | 73 |
| Example 17 | 73 |
| Example 18 | 71 |
| Example 19 | 71 |
| Example 20 | 69 |
| Example 21 | 65 |
| Example 22 | 64 |
| Example 23 | 63 |
| Example 24 | 62 |
| Example 25 | 62 |
| Example 26 | 61 |
| Example 27 | 59 |
| Example 28 | 59 |
| Example 29 | 58 |
| Example 30 | 56 |
| Example 31 | 56 |
| Example 32 | 54 |
| Example 33 | 54 |
| Example 34 | 53 |
| Example 35 | 53 |
| Example 36 | 52 |
| Example 37 | 52 |
| Example 38 | 52 |
| Example 39 | 48 |
| Example 40 | 47 |
| Example 41 | 46 |
| Example 42 | 46 |
| Example 43 | 46 |
| Example 44 | 44 |
| Example 45 | 43 |
| Example 46 | 42 |
| Example 47 | 41 |
| Example 48 | 41 |

| Compound | ORL-1 receptor [1 µM], % inhibition |
|---|---|
| Example 1 | 98 |
| Example 2 | 66 |
| Example 3 | 89 |
| Example 4 | 86 |
| Example 5 | 54 |
| Example 6 | 59 |
| Example 7 | 96 |

Parenteral Solution of a Substituted cyclohexyl-1,4-diamine Derivative According to the Invention 38 g of one of the substituted cyclohexyl-1,4-diamine derivatives according to the invention, here Example 1, are dissolved in 1 l of water for injection purposes at room temperature and then adjusted to isotonic conditions by addition of anhydrous glucose for injection purposes.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A cyclohexyl-1,4-diamine compound corresponding to formula I

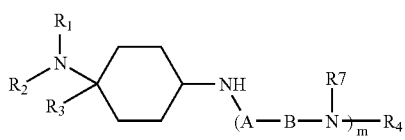

wherein
$R^1$ and $R^2$, independently of one another, represent H; $C_{1-5}$-alkyl, in each case saturated or unsaturated, branched or unbranched, mono- or poly-substituted or unsubstituted; $C_{3-8}$-cycloalkyl, in each case mono- or poly-substituted or unsubstituted; or aryl, $C_{3-8}$-cycloalkyl or heteroaryl bonded via $C_{1-3}$-alkyl, in each case mono- or poly-substituted or unsubstituted;
or $R^1$ and $R^2$ together represent $CH_2CH_2OCH_2CH_2$, $CH_2CH_2NR^{10}CH_2CH_2$ or $(CH_2)_{3-6}$,
wherein $R^{10}$ represents H; $C_{1-5}$-alkyl, in each case saturated or unsaturated, branched or unbranched, mono- or poly-substituted or unsubstituted; $C_{3-8}$-cycloalkyl, in each case mono- or poly-substituted or unsubstituted; aryl or heteroaryl, in each case mono- or poly-substituted or unsubstituted; or aryl, $C_{3-8}$-cycloalkyl or heteroaryl bonded via $C_{1-3}$-alkyl, in each case mono- or poly-substituted or unsubstituted; C(O)phenyl, C(O)heteroaryl, C(O)$C_{1-5}$-alkyl, in each case substituted or unsubstituted;
$R^3$ represents $C_{1-5}$-alkyl, in each case saturated or unsaturated, branched or unbranched, mono- or poly-substituted or unsubstituted; $C_{3-8}$-cycloalkyl, in each case mono- or poly-substituted or unsubstituted; aryl or heteroaryl, in each case unsubstituted or mono- or poly-substituted; aryl, heteroaryl or $C_{3-8}$-cycloalkyl bonded via a $C_{1-3}$-alkyl group, in each case unsubstituted or mono- or poly-substituted;
m represents 1, 2 or 3;
A represents C(O) or $SO_2$;
each B independently represents $(CR^5R^6)_n$ or aryl, heteroaryl or $C_{3-8}$-cycloalkyl, in each case mono- or poly-substituted or unsubstituted; or aryl, $C_{3-8}$-cycloalkyl or heteroaryl bonded via $C_{1-3}$-alkyl, wherein an individual carbon atom of the $C_{1-3}$-alkyl may be replaced by O, in each case mono- or poly-substituted or unsubstituted, wherein one $C_{1-3}$-alkyl may link the aryl, $C_{3-8}$-cycloalkyl or heteroaryl to A and N, or a first $C_{1-3}$-alkyl may link the aryl, $C_{3-8}$-cycloalkyl or heteroaryl to A and a second $C_{1-3}$-alkyl may link the aryl, $C_{3-8}$-cycloalkyl or heteroaryl to N; where n =1, 2, 3, 4 or 5;
$R^4$ represents C(O)$R^9$ or $SO_2R^8$;
$R^5$ and $R^6$ independently represent H, $C_{1-5}$-alkyl, in each case saturated or unsaturated, branched or unbranched, mono- or poly-substituted or unsubstituted; $C_{3-8}$-cycloalkyl, in each case mono- or poly-substituted or unsubstituted; aryl or heteroaryl, in each case mono- or poly-substituted or unsubstituted; or aryl, $C_{3-8}$-cycloalkyl or heteroaryl bonded via $C_{1-3}$-alkyl, in each case mono- or poly-substituted or unsubstituted;
$R^7$ represents H or, with B, forms a five-, six- or seven-membered ring which may be saturated or unsaturated but not aromatic and which may be part of a polycyclic system;
$R^8$ represents $C_{1-5}$-alkyl, in each case saturated or unsaturated, branched or unbranched, mono- or poly-substituted or unsubstituted; $C_{3-8}$-cycloalkyl, in each case mono- or poly-substituted or unsubstituted; aryl or heteroaryl, in each case mono- or poly-substituted or unsubstituted; or aryl, $C_{3-8}$-cycloalkyl or heteroaryl bonded via $C_{1-3}$-alkyl, in each case mono- or poly-substituted or unsubstituted;
$R^9$ represents $OR^{11}$, $C_{1-5}$-alkyl, in each case saturated or unsaturated, branched or unbranched, mono- or poly-substituted or unsubstituted; $C_{3-8}$-cycloalkyl, in each case mono- or poly-substituted or unsubstituted; aryl or heteroaryl, in each case mono- or poly-substituted or unsubstituted; or aryl, $C_{3-8}$-cycloalkyl or heteroaryl bonded via $C_{1-3}$-alkyl, in each case mono- or poly-substituted or unsubstituted;
$R^{11}$ represents $C_{1-5}$-alkyl, in each case saturated or unsaturated, branched or unbranched, mono- or poly-substituted or unsubstituted; $C_{3-8}$-cycloalkyl, in each case mono- or poly-substituted or unsubstituted; aryl or heteroaryl, in each case mono- or poly-substituted or unsubstituted; or aryl, $C_{3-8}$-cycloalkyl or heteroaryl bonded via $C_{1-3}$-alkyl, in each case mono- or poly-substituted or unsubstituted;
or an acid, base or a physiologically acceptable salt thereof.

2. The compound of claim 1, wherein said compound is present in the form of a pure enantiomer or pure diastereoisomer.

3. The compound of claim 1, wherein said compound is present in the form of a mixture of stereoisomers.

4. The compound of claim 1, wherein said compound is present in the form of a racemic mixture.

5. A cyclohexyl-1,4-diamine compound according to claim 1, wherein
$R^1$ and $R^2$, independently of one another, represent H; $C_{1-5}$-alkyl, saturated or unsaturated, branched or unbranched, mono- or poly-substituted or unsubstituted; or $R^1$ and $R^2$ together form a ring and represent $CH_2CH_2OCH_2CH_2$, $CH_2CH_2NR^{10}CH_2CH_2$ or $(CH_2)_{3-6}$.

6. A cyclohexyl-1,4-diamine compound according to claim 1, wherein
$R^1$ and $R^2$, independently of one another, represent $CH_3$ or H, wherein $R^1$ and $R^2$ are not both H, or $R^1$ and $R^2$ together form a ring and represent $CH_2CH_2OCH_2CH_2$, $(CH_2)_4$, $(CH_2)_5$ or $(CH_2)_6$.

7. A cyclohexyl-1,4-diamine compound according to claim 1, wherein
$R^3$ represents cyclopentyl, cyclohexyl, phenyl, benzyl, naphthyl, anthracenyl, thiophenyl, benzothiophenyl, furyl, benzofuranyl, benzodioxolanyl, indolyl, indanyl, benzodioxanyl, pyrrolyl, pyridyl, pyrimidyl or pyrazinyl, in each case unsubstituted or mono- or poly-substituted; $C_{5-6}$-cycloalkyl, phenyl, naphthyl, anthracenyl, thiophenyl, benzothiophenyl, pyridyl, furyl, benzofuranyl, benzodioxolanyl, indolyl, indanyl, benzodioxanyl, pyrrolyl, pyrimidyl or pyrazinyl bonded via a saturated, unbranched $C_{1-2}$-alkyl group, in each case unsubstituted or mono- or poly-substituted.

8. A cyclohexyl-1,4-diamine compound according to claim 1, wherein
R$^3$ represents phenyl, furyl, thiophenyl, naphthyl, benzyl, benzofuranyl, indolyl, indanyl, benzodioxanyl, benzodioxolanyl, pyridyl, pyrimidyl, pyrazinyl or benzothiophenyl, in each case unsubstituted or mono- or poly-substituted; phenyl, furyl or thiophenyl bonded via a saturated, unbranched C$_{1-2}$-alkyl group, in each case unsubstituted or mono- or poly-substituted.

9. A cyclohexyl-1,4-diamine compound according to claim 1, wherein
R$^3$ represents phenyl, phenethyl, thiophenyl, pyridyl or benzyl, in each case substituted or unsubstituted.

10. A cyclohexyl-1,4-diamine compound according to claim 1, wherein
B represents (CR$^5$R$^6$)$_n$.

11. A cyclohexyl-1,4-diamine compound according to claim 1, wherein B represents aryl, heteroaryl or C$_{3-8}$-cycloalkyl, in each case mono- or poly-substituted or unsubstituted; or aryl bonded via C$_{13}$-alkyl, wherein an individual carbon atom of the alkyl chain may be replaced by O, in each case mono- or poly-substituted or unsubstituted, wherein a C$_{1-3}$-alkyl chain may link the cyclic radical to A or N or both A and N.

12. A cyclohexyl-1,4-diamine compound according to claim 1, wherein R$^5$ and R$^6$ represent H, C$_{1-5}$-alkyl, in each case saturated or unsaturated, branched or unbranched, mono- or poly-substituted or unsubstituted; aryl, in each case mono- or poly-substituted or unsubstituted; or aryl or C$_{3-8}$-cycloalkyl bonded via C$_{1-2}$-alkyl, in each case mono- or poly-substituted or unsubstituted.

13. A cyclohexyl-1,4-diamine compound according to claim 1, wherein
R$^5$ and R$^6$ represent H, C$_{1-5}$-alkyl, benzyl or phenyl.

14. A cyclohexyl-1,4-diamine compound according to claim 1, wherein
R$^7$ represents H.

15. A cyclohexyl-1,4-diamine compound according to claim 1, wherein
R$^4$ represents SO$_2$R$^8$, and
R$^8$ represents C$_{1-5}$-alkyl, cyclohexyl, cyclopentyl, cyclobutyl, cycloheptyl, cyclooctyl, phenyl, benzyl, naphthyl, thiophenyl, benzothiophenyl, furanyl, pyrazolyl, benzofuranyl, benzodioxolanyl, isoquinolinyl, indolyl, pyrrolyl, pyridyl, pyrimidyl or pyrazinyl, in each case unsubstituted or mono- or poly-substituted; phenyl, naphthyl, thiophenyl, benzothiophenyl, pyridyl, furyl, benzofuranyl, indolyl, benzodioxanyl, pyrrolyl, pyrimidyl or pyrazinyl bonded via a saturated, unbranched substituted or unsubstituted C$_{1-2}$-alkyl group, in each case unsubstituted or mono- or poly-substituted.

16. A cyclohexyl-1,4-diamine compound according to claim 1, wherein
R$^4$ represents SO$_2$R$^8$, and
R$^8$ represents phenyl, C$_{1-5}$-alkyl, branched or unbranched, saturated or unsaturated, or benzyl, in each case unsubstituted or mono- or poly-substituted.

17. A cyclohexyl-1,4-diamine compound according to claim 1, wherein
R$^{11}$ represents C$_{1-5}$-alkyl, cyclohexyl, cyclopentyl, cycloheptyl, cyclooctyl, phenyl, benzyl, naphthyl, thiophenyl, benzothiophenyl, furanyl, pyrazolyl, benzofuranyl, indolyl, pyrrolyl, pyridyl, pyrimidyl or pyrazinyl, in each case unsubstituted or mono- or poly-substituted; phenyl, naphthyl, thiophenyl, benzothiophenyl, pyridyl, furyl, benzofuranyl, indolyl, pyrrolyl, pyrimidyl or pyrazinyl bonded via a saturated, unbranched substituted or unsubstituted C$_{1-2}$-alkyl group, in each case unsubstituted or mono- or poly-substituted.

18. A cyclohexyl-1,4-diamine compound according to claim 1, wherein
R$^{11}$ represents phenyl, C$_{1-5}$-alkyl, branched or unbranched, saturated or unsaturated, benzyl or methylfluorenyl, in each case unsubstituted or mono- or poly-substituted.

19. A cyclohexyl-1,4-diamine compound according to claim 1, wherein said compound is selected from the group consisting of:
({1-[4-dimethylamino-4-(3-fluoro-phenyl)-cyclohexylcarbamoyl]-3-methyl-butylcarbamoyl}-methyl)-carbamic acid benzyl ester;
{2-[4-dimethylamino-4-(3-fluoro-phenyl)-cyclohexylcarbamoyl]-ethyl}-carbamic acid tert.-butyl ester;
{[1-(4-dimethylamino-4-thiophen-2-yl-cyclohexylcarbamoyl)-3-methyl-butylcarbamoyl]-methyl}-carbamic acid benzyl ester;
N-(4-dimethylamino-4-thiophen-2-yl-cyclohexyl)-3-phenyl-2-(tolyl-4-sulfonylamino)-propionamide;
[1-(4-dimethylamino-4-thiophen-2-yl-cyclohexylcarbamoyl)-ethyl]-carbamic acid benzyl ester;
N-(4-dimethylamino-4-pyridin-2-yl-cyclohexyl)-3-phenyl-2-(tolyl-4-sulfonyl-amino)-propionamide;
{[1-(4-dimethylamino-4-phenyl-cyclohexylcarbamoyl)-3-methyl-butyl-carbamoyl]-methyl}-carbamic acid benzyl ester;
{[4-dimethylamino-4-(2-methyl-benzyl)-cyclohexylcarbamoyl]-phenyl-methyl}-carbamic acid benzyl ester;
[(4-azepan-1-yl-4-benzyl-cyclohexylcarbamoyl)-phenyl-methyl]-carbamic acid benzyl ester;
{[4-(2-chloro-benzyl)-4-dimethylamino-cyclohexylcarbamoyl]-phenyl-methyl}-carbamic acid benzyl ester;
{1-[4-(2-chloro-benzyl)-4-dimethylamino-cyclohexylcarbamoyl]-ethyl}-carbamic acid benzyl ester;
{[1-(4-benzyl-4-dimethylamino-cyclohexylcarbamoyl)-3-methyl-butyl-carbamoyl]-methyl}-carbamic acid benzyl ester;
{1-[4-dimethylamino-4-(2-methyl-benzyl)-cyclohexylcarbamoyl]-2-phenyl-ethyl}-carbamic acid benzyl ester;
({1-[4-dimethylamino-4-(2-fluoro-benzyl)-cyclohexylcarbamoyl]-3-methyl-butylcarbamoyl}-methyl)-carbamic acid benzyl ester;
N-{1-[4-dimethylamino-4-(4-fluoro-benzyl)-cyclohexylcarbamoyl]-3-methyl-butyl}-benzamide;
{1-[4-(2-chloro-benzyl)-4-dimethylamino-cyclohexylcarbamoyl]-2-phenyl-ethyl}-carbamic acid tert.-butyl ester;
{1-[4-dimethylamino-4-(2-fluoro-benzyl)-cyclohexylcarbamoyl]-2-phenyl-ethyl}-carbamic acid tert.-butyl ester;
({1-[4-dimethylamino-4-(3-methyl-benzyl)-cyclohexylcarbamoyl]-3-methyl-butylcarbamoyl}-methyl)-carbamic acid benzyl ester;
({1-[4-dimethylamino-4-(3-fluoro-benzyl)-cyclohexylcarbamoyl]-3-methyl-butylcarbamoyl}-methyl)-carbamic acid benzyl ester;
{[1-(4-dimethylamino-4-phenethyl-cyclohexylcarbamoyl)-3-methyl-butyl-carbamoyl]-methyl}-carbamic acid benzyl ester;
2-acetylamino-hexanoic acid [4-(2-chloro-benzyl)-4-dimethylamino-cyclo-hexyl]-amide;
N-[4-(2-chloro-benzyl)-4-dimethylamino-cyclohexyl]-3-phenyl-2-(tolyl-4-sulfonylamino)-propionamide;

3-tert.-butoxycarbonylamino-N-[4-(2-chloro-benzyl)-4-dimethylamino-cyclohexyl]-succinic acid cyclohexyl ester;
{1-[4-dimethylamino-4-(3-methyl-benzyl)-cyclohexylcarbamoyl]-2-phenyl-ethyl}-carbamic acid tert.-butyl ester;
({1-[4-dimethylamino-4-(2-methyl-benzyl)-cyclohexylcarbamoyl]-3-methyl-butylcarbamoyl}-methyl)-carbamic acid benzyl ester;
{1-[4-dimethylamino-4-(2-methyl-benzyl)-cyclohexylcarbamoyl]-ethyl}-carbamic acid benzyl ester;
{1-[4-dimethylamino-4-(2-methyl-benzyl)-cyclohexylcarbamoyl]-2-phenyl-ethyl}-carbamic acid tert.-butyl ester;
({1-[4-(3-chloro-benzyl)-4-dimethylamino-cyclohexylcarbamoyl]-3-methyl-butylcarbamoyl}-methyl)-carbamic acid benzyl ester;
({1-[4-dimethylamino-4-(4-methyl-benzyl)-cyclohexylcarbamoyl]-3-methyl-butylcarbamoyl}-methyl)-carbamic acid benzyl ester;
[1-(4-dimethylamino-4-phenethyl-cyclohexylcarbamoyl)-ethyl]-carbamic acid benzyl ester;
{1-[4-dimethylamino-4-(3-methyl-benzyl)-cyclohexylcarbamoyl]-2-hydroxy-ethyl}-carbamic acid tert.-butyl ester;
[5-(4-benzyl-4-dimethylamino-cyclohexylcarbamoyl)-pentyl]-carbamic acid benzyl ester;
{1-[4-(3-chloro-benzyl)-4-dimethylamino-cyclohexylcarbamoyl]-2-hydroxy-ethyl}-carbamic acid tert.-butyl ester;
N-[4-dimethylamino-4-(2-methyl-benzyl)-cyclohexyl]-3-phenyl-2-(tolyl-4-sulfonylamino)-propionamide;
4-chloro-N-[2-(4-{1-[4-dimethylamino-4-(2-methyl-benzyl)-cyclohexylcarbamoyl]-1-methyl-ethoxy}-phenyl)-ethyl]-benzamide;
[1-(4-benzyl-4-dimethylamino-cyclohexylcarbamoyl)-2-phenyl-ethyl]-carbamic acid tert.-butyl ester;
{1-[4-dimethylamino-4-(3-fluoro-benzyl)-cyclohexylcarbamoyl]-2-phenyl-ethyl}-carbamic acid tert.-butyl ester;
({1-[4-(4-chloro-benzyl)-4-dimethylamino-cyclohexylcarbamoyl]-3-methyl-butylcarbamoyl}-methyl)-carbamic acid benzyl ester;
{1-[4-dimethylamino-4-(4-fluoro-benzyl)-cyclohexylcarbamoyl]-2-methyl-propyl}-carbamic acid 9H-fluoren-9-ylmethyl ester;
{1-[4-dimethylamino-4-(3-methyl-benzyl)-cyclohexylcarbamoyl]-ethyl}-carbamic acid benzyl ester;
{1-[4-dimethylamino-4-(2-methyl-benzyl)-cyclohexylcarbamoyl]-2-methyl-propyl}-carbamic acid 9H-fluoren-9-ylmethyl ester;
{1-[4-(3-chloro-benzyl)-4-dimethylamino-cyclohexylcarbamoyl]-ethyl}-carbamic acid benzyl ester;
{[1-(4-benzyl-4-piperidin-1-yl-cyclohexylcarbamoyl)-3-methyl-butyl-carbamoyl]-methyl}-carbamic acid benzyl ester;
{5-[4-dimethylamino-4-(4-methyl-benzyl)-cyclohexylcarbamoyl]-pentyl}-carbamic acid benzyl ester;
{[3-methyl-1-(4-phenyl-4-piperidin-1-yl-cyclohexylcarbamoyl)-butyl-carbamoyl]-methyl}-carbamic acid benzyl ester;
{1-[4-dimethylamino-4-(4-methyl-benzyl)-cyclohexylcarbamoyl]-2-hydroxy-ethyl}-carbamic acid tert.-butyl ester;
[1-(4-benzyl-4-dimethylamino-cyclohexylcarbamoyl)-ethyl]-carbamic acid benzyl ester;
{1-[4-dimethylamino-4-(4-methyl-benzyl)-cyclohexylcarbamoyl)-ethyl}-carbamic acid benzyl ester;
[1-(4-benzyl-4-piperidin-1-yl-cyclohexylcarbamoyl)-3-carbamoyl-propyl]-carbamic acid tert.-butyl ester;
2-acetylamino-pent-4-enoic acid [4-(2-chloro-benzyl)-4-dimethylamino-cyclohexyl]-amide;
[2-hydroxy-1-(4-phenyl-4-piperidin-1-yl-cyclohexylcarbamoyl)-ethyl]-carbamic acid tert.-butyl ester;
4-chloro-N-[2-(4-{1-[4-(2-chloro-benzyl)-4-dimethylamino-cyclohexyl-carbamoyl]-1-methyl-ethoxy}-phenyl)-ethyl]-benzamide;
{3-carbamoyl-1-[4-(4-chloro-benzyl)-4-dimethylamino-cyclohexylcarbamoyl]-propyl}-carbamic acid tert.-butyl ester;
[1-(4-benzyl-4-piperidin-1-yl-cyclohexylcarbamoyl)-ethyl]-carbamic acid benzyl ester;
[2-(4-dimethylamino-4-phenethyl-cyclohexylcarbamoyl)ethyl]-carbamic acid tert.-butyl ester;
{1-[4-(4-chloro-benzyl)-4-dimethylamino-cyclohexylcarhamoyl]-ethyl}-carbamic acid benzyl ester;
{1-[4-dimethylamino-4-(4-methyl-benzyl)-cyclohexylcarbamoyl]-2-phenyl-ethyl}-carbamic acid tert.-butyl ester;
[1-(4-morpholin-4-yl-4-phenyl-cyclohexylcarbamoyl)-2-phenyl-ethyl]-carbamic acid tert.-butyl ester;
{1-[4-dimethylamino-4-(3-fluoro-benzyl)-cyclohexylcarbamoyl]-ethyl}-carbamic acid benzyl ester;
{2-[4-(4-chloro-benzyl)-4-dimethylamino-cyclohexylcarbamoyl]-ethyl}-carbamic acid tert.-butyl ester;
[2-hydroxy-1-(4-morpholin-4-yl-4-phenyl-cyclohexylcarbamoyl)-ethyl]-carbamic acid tert.-butyl ester;
{1-[4-(4-chloro-benzyl)-4-dimethylamino-cyclohexylcarbamoyl]-2-hydroxy-ethyl}-carbamic acid tert.-butyl ester;
{2-[4-dimethylamino-4-(4-methyl-benzyl)-cyclohexylcarbamoyl]-ethyl}-carbamic acid tert.-butyl ester;
{1-[4-(4-chloro-benzyl)-4-dimethylamino-cyclohexylcarbamoyl]-2-phenyl-ethyl}-carbamic acid tert.-butyl ester;
[1-(4-azepan-1-yl-4-benzyl-cyclohexylcarbamoyl)-2-phenyl-ethyl]-carbamic acid tert.-butyl ester;
{2-[4-dimethylamino-4-(3-fluoro-benzyl)-cyclohexylcarbamoyl]-ethyl}-carbamic acid tert.-butyl ester;
[1-(4-morpholin-4-yl-4-phenyl-cyclohexylcarbamoyl)-ethyl]-carbamic acid benzyl ester;
[1-(4-benzyl-4-piperidin-1-yl-cyclohexylcarbamoyl)-2-hydroxy-ethyl]-carbamic acid tert.-butyl ester;
2-(2,2,2-trifluoro-acetyl)-1,2,3,4-tetrahydro-isoquinoline-7-sulfonic acid (4-benzyl-4-pyrrolidin-1-yl-cyclohexyl)-amide;
[2-phenyl-1-(4-phenyl-4-piperidin-1-yl-cyclohexylcarbamoyl)-ethyl]-carbamic acid tert.-butyl ester; and
{[3-methyl-1-(4-morpholin-4-yl-4-phenyl-cyclohexylcarbamoyl)-butyl-carbamoyl]-methyl}-carbamic acid benzyl ester.

20. A process for preparing a cyclohexyl-1,4-diamine compound corresponding to formula I

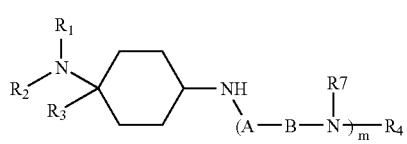

wherein

R¹ and R², independently of one another, represent H; $C_{1-5}$-alkyl, in each case saturated or unsaturated, branched or unbranched, mono- or poly-substituted or unsubstituted; $C_{3-8}$-cycloalkyl, in each case mono- or poly-substituted or unsubstituted; or aryl, $C_{3-8}$-cycloalkyl or heteroaryl bonded via $C_{1-3}$-alkyl, in each case mono- or poly-substituted or unsubstituted;

or R¹ and R² together represent $CH_2CH_2OCH_2CH_2$, $CH_2CH_2NR^{10}CH_2CH_2$ or $(CH_2)_{3-6}$, wherein $R^{10}$ represents H; $C_{1-5}$-alkyl, in each case saturated or unsaturated, branched or unbranched, mono- or poly-substituted or unsubstituted; $C_{3-8}$-cycloalkyl, in each case mono- or poly-substituted or unsubstituted; aryl or heteroaryl, in each case mono- or poly-substituted or unsubstituted; or aryl, $C_{3-8}$-cycloalkyl or heteroaryl bonded via $C_{1-3}$-alkyl, in each case mono- or poly-substituted or unsubstituted; C(O)phenyl, C(O)heteroaryl, $C(O)C_{1-5}$-alkyl, in each case substituted or unsubstituted;

R³ represents $C_{1-5}$-alkyl, in each case saturated or unsaturated, branched or unbranched, mono- or poly-substituted or unsubstituted; $C_{3-8}$-cycloalkyl, in each case mono- or poly-substituted or unsubstituted; aryl or heteroaryl, in each case unsubstituted or mono- or poly-substituted; aryl, heteroaryl or $C_{3-8}$-cycloalkyl bonded via a $C_{1-3}$-alkyl group, in each case unsubstituted or mono- or poly-substituted;

m represents 1, 2 or 3;

A represents C(O) or $SO_2$;

each B independently represents $(CR^5R^6)_n$ or aryl, heteroaryl or $C_{3-8}$-cycloalkyl, in each case mono- or poly-substituted or unsubstituted; or aryl, $C_{3-8}$-cycloalkyl or heteroaryl bonded via $C_{1-3}$-alkyl, wherein an individual carbon atom of the $C_{1-3}$-alkyl may be replaced by O, in each case mono- or poly-substituted or unsubstituted, wherein one $C_{1-3}$-alkyl may link the aryl, $C_{3-8}$-cycloalkyl or heteroaryl to A and N, or a first $C_{1-3}$-alkyl may link the aryl, $C_{3-8}$-cycloalkyl or heteroaryl to A and a second $C_{1-3}$-alkyl may link the aryl, $C_{3-8}$-cycloalkyl or heteroaryl to N; where n=1, 2, 3, 4 or 5;

R⁴ represents $C(O)R^9$ or $SO_2R^8$;

R⁵ and R⁶ independently represent H, $C_{1-5}$-alkyl, in each case saturated or unsaturated, branched or unbranched, mono- or poly-substituted or unsubstituted; $C_{3-8}$-cycloalkyl, in each case mono- or poly-substituted or unsubstituted; aryl or heteroaryl, in each case mono- or poly-substituted or unsubstituted; or aryl, $C_{3-8}$-cycloalkyl or heteroaryl bonded via $C_{1-3}$-alkyl, in each case mono- or poly-substituted or unsubstituted;

R⁷ represents H or, with B, forms a five-, six- or seven-membered ring which may be saturated or unsaturated but not aromatic and which may be part of a polycyclic system;

R⁸ represents $C_{1-5}$-alkyl, in each case saturated or unsaturated, branched or unbranched, mono- or poly-substituted or unsubstituted; $C_{3-8}$-cycloalkyl, in each case mono- or poly-substituted or unsubstituted; aryl or heteroaryl, in each case mono- or poly-substituted or unsubstituted; or aryl, $C_{3-8}$-cycloalkyl or heteroaryl bonded via $C_{1-3}$-alkyl, in each case mono- or poly-substituted or unsubstituted;

R⁹ represents $OR^{11}$, $C_{1-5}$-alkyl, in each case saturated or unsaturated, branched or unbranched, mono- or poly-substituted or unsubstituted; $C_{3-8}$-cycloalkyl, in each case mono- or poly-substituted or unsubstituted; aryl or heteroaryl, in each case mono- or poly-substituted or unsubstituted; or aryl, $C_{3-8}$-cycloalkyl or heteroaryl bonded via $C_{1-3}$-alkyl, in each case mono- or poly-substituted or unsubstituted;

$R^{11}$ represents $C_{1-5}$-alkyl, in each case saturated or unsaturated, branched or unbranched, mono- or poly-substituted or unsubstituted; $C_{3-8}$-cycloalkyl, in each case mono- or poly-substituted or unsubstituted; aryl or heteroaryl, in each case mono- or poly-substituted or unsubstituted; or aryl, $C_{3-8}$-cycloalkyl or heteroaryl bonded via $C_{1-3}$-alkyl, in each case mono- or poly-substituted or unsubstituted;

or a physiologically acceptable salt thereof;

said process comprising the steps of:

linking a cyclohexane-1,4-diamine compound to a carboxylic acid or sulfonic acid corresponding to formula II

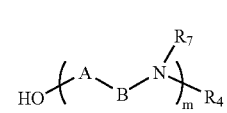

II by adding coupling reagents or by activating the acid.

21. The process of claim 20, wherein said process comprises the step of producing an acid chloride.

22. A pharmaceutical formulation comprising at least one cyclohexyl-1,4-diamine compound corresponding to formula I

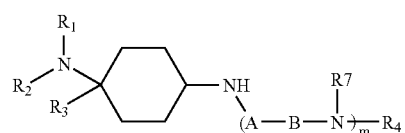

I wherein

R¹ and R², independently of one another, represent H; $C_{1-5}$-alkyl, in each case saturated or unsaturated, branched or unbranched, mono- or poly-substituted or unsubstituted; $C_{3-8}$-cycloalkyl, in each case mono- or poly-substituted or unsubstituted; or aryl, $C_{3-8}$-cycloalkyl or heteroaryl bonded via $C_{1-3}$-alkyl, in each case mono- or poly-substituted or unsubstituted;

or R¹ and R² together represent $CH_2CH_2OCH_2CH_2$, $CH_2CH_2NR^{10}CH_2CH_2$ or $(CH_2)_{3-6}$, wherein $R^{10}$ represents H; $C_{1-5}$-alkyl, in each case saturated or unsaturated, branched or unbranched, mono- or poly-substituted or unsubstituted; $C_{3-8}$-cycloalkyl, in each case mono- or poly-substituted or unsubstituted; aryl or heteroaryl, in each case mono- or poly-substituted or unsubstituted; or aryl, $C_{3-8}$-cycloalkyl or heteroaryl bonded via $C_{1-3}$-alkyl, in each case mono- or poly-substituted or unsubstituted; C(O)phenyl, C(O)heteroaryl, $C(O)C_{1-5}$-alkyl, in each case substituted or unsubstituted;

R³ represents $C_{1-5}$-alkyl, in each case saturated or unsaturated, branched or unbranched, mono- or poly-substituted or unsubstituted; $C_{3-8}$-cycloalkyl, in each case mono- or poly-substituted or unsubstituted; aryl or heteroaryl, in each case unsubstituted or mono- or poly-substituted; aryl, heteroaryl or $C_{3-8}$-cycloalkyl bonded via a $C_{1-3}$-alkyl group, in each case unsubstituted or mono- or poly-substituted;

m represents 1, 2 or 3;

A represents $C(O)$ or $SO_2$;

each B independently represents $(CR^5R^6)_n$ or aryl, heteroaryl or $C_{3-8}$-cycloalkyl, in each case mono- or poly-substituted or unsubstituted; or aryl, $C_{3-8}$-cycloalkyl or heteroaryl bonded via $C_{1-3}$-alkyl, wherein an individual carbon atom of the $C_{1-3}$-alkyl may be replaced by O, in each case mono- or poly-substituted or unsubstituted, wherein one $C_{1-3}$-alkyl may link the aryl, $C_{3-8}$-cycloalkyl or heteroaryl to A and N, or a first $C_{1-3}$-alkyl may link the aryl, $C_{3-8}$-cycloalkyl or heteroaryl to A and a second $C_{1-3}$-alkyl may link the aryl, $C_{3-8}$-cycloalkyl or heteroaryl to N; where n=1, 2, 3, 4 or 5;

$R^4$ represents $C(O)R^9$ or $SO_2R^8$;

$R^5$ and $R^6$ independently represent H, $C_{1-5}$-alkyl, in each case saturated or unsaturated, branched or unbranched, mono- or poly-substituted or unsubstituted; $C_{3-8}$-cycloalkyl, in each case mono- or poly-substituted or unsubstituted; aryl or heteroaryl, in each case mono- or poly-substituted or unsubstituted; or aryl, $C_{3-8}$-cycloalkyl or heteroaryl bonded via $C_{1-3}$-alkyl, in each case mono- or poly-substituted or unsubstituted;

$R^7$ represents H or, with B, forms a five-, six- or seven-membered ring which may be saturated or unsaturated but not aromatic and which may be part of a polycyclic system;

$R^8$ represents $C_{1-5}$-alkyl, in each case saturated or unsaturated, branched or unbranched, mono- or poly-substituted or unsubstituted; $C_{3-8}$-cycloalkyl, in each case mono- or poly-substituted or unsubstituted; aryl or heteroaryl, in each case mono- or poly-substituted or unsubstituted; or aryl, $C_{3-8}$-cycloalkyl or heteroaryl bonded via $C_{1-3}$-alkyl, in each case mono- or poly-substituted or unsubstituted;

$R^9$ represents $OR^{11}$, $C_{1-5}$-alkyl, in each case saturated or unsaturated, branched or unbranched, mono- or poly-substituted or unsubstituted; $C_{3-8}$-cycloalkyl, in each case mono- or poly-substituted or unsubstituted; aryl or heteroaryl, in each case mono- or poly-substituted or unsubstituted; or aryl, $C_{3-8}$-cycloalkyl or heteroaryl bonded via $C_{1-3}$-alkyl, in each case mono- or poly-substituted or unsubstituted;

$R^{11}$ represents $C_{1-5}$-alkyl, in each case saturated or unsaturated, branched or unbranched, mono- or poly-substituted or unsubstituted; $C_{3-8}$-cycloalkyl, in each case mono- or poly-substituted or unsubstituted; aryl or heteroaryl, in each case mono- or poly-substituted or unsubstituted; or aryl, $C_{3-8}$-cycloalkyl or heteroaryl bonded via $C_{1-3}$-alkyl, in each case mono- or poly-substituted or unsubstituted;

or a physiologically acceptable salt thereof, and one or more physiologically acceptable auxiliary substances.

23. A method of producing a pharmaceutical formulation comprising the steps of combining a pharmaceutically effective amount of a cyclohexyl-1,4-diamine compound corresponding to formula I

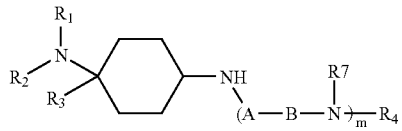

wherein $R^1$ and $R^2$, independently of one another, represent H; $C_{1-5}$-alkyl, in each case saturated or unsaturated, branched or unbranched, mono- or poly-substituted or unsubstituted; $C_{3-8}$-cycloalkyl, in each case mono- or poly-substituted or unsubstituted; or aryl, $C_{3-8}$-cycloalkyl or heteroaryl bonded via $C_{1-3}$-alkyl, in each case mono- or poly-substituted or unsubstituted;

or $R^1$ and $R^2$ together represent $CH_2CH_2OCH_2CH_2$, $CH_2CH_2NR^{10}CH_2CH_2$ or $(CH_2)_{3-6}$, wherein $R^{10}$ represents H; $C_{1-5}$-alkyl, in each case saturated or unsaturated, branched or unbranched, mono- or poly-substituted or unsubstituted; $C_{3-8}$-cycloalkyl, in each case mono- or poly-substituted or unsubstituted; aryl or heteroaryl, in each case mono- or poly-substituted or unsubstituted; or aryl, $C_{3-8}$-cycloalkyl or heteroaryl bonded via $C_{1-3}$-alkyl, in each case mono- or poly-substituted or unsubstituted; $C(O)$phenyl, $C(O)$heteroaryl, $C(O)C_{1-5}$-alkyl, in each case substituted or unsubstituted;

$R^3$ represents $C_{1-5}$-alkyl, in each case saturated or unsaturated, branched or unbranched, mono- or poly-substituted or unsubstituted; $C_{3-8}$-cycloalkyl, in each case mono- or poly-substituted or unsubstituted; aryl or heteroaryl, in each case unsubstituted or mono- or poly-substituted; aryl, heteroaryl or $C_{3-8}$-cycloalkyl bonded via a $C_{1-3}$-alkyl group, in each case unsubstituted or mono- or poly-substituted;

m represents 1, 2 or 3;

A represents $C(O)$ or $SO_2$;

each B independently represents $(CR^5R^6)_n$ or aryl, heteroaryl or $C_{3-8}$-cycloalkyl, in each case mono- or poly-substituted or unsubstituted; or aryl, $C_{3-8}$-cycloalkyl or heteroaryl bonded via $C_{1-3}$-alkyl, wherein an individual carbon atom of the $C_{1-3}$-alkyl may be replaced by O, in each case mono- or poly-substituted or unsubstituted, wherein one $C_{1-3}$-alkyl may link the aryl, $C_{3-8}$-cycloalkyl or heteroaryl to A and N, or a first $C_{1-3}$-alkyl may link the aryl, $C_{3-8}$-cycloalkyl or heteroaryl to A and a second $C_{1-3}$-alkyl may link the aryl, $C_{3-8}$-cycloalkyl or heteroaryl to N; where n=1, 2, 3, 4 or 5:

$R^4$ represents $C(O)R^9$ or $SO_2R^8$;

$R^5$ and $R^6$ independently represent H, $C_{1-5}$-alkyl, in each case saturated or unsaturated, branched or unbranched, mono- or poly-substituted or unsubstituted; $C_{3-8}$-cycloalkyl, in each case mono- or poly-substituted or unsubstituted; aryl or heteroaryl, in each case mono- or poly-substituted or unsubstituted; or aryl, $C_{3-8}$-cycloalkyl or heteroaryl bonded via $C_{1-3}$-alkyl, in each case mono- or poly-substituted or unsubstituted;

$R^7$ represents H or, with B, forms a five-, six- or seven-membered ring which may be saturated or unsaturated but not aromatic and which may be part of a polycyclic system;

$R^8$ represents $C_{1-5}$-alkyl, in each case saturated or unsaturated, branched or unbranched, mono- or poly-substituted or unsubstituted; $C_{3-8}$-cycloalkyl, in each case mono- or poly-substituted or unsubstituted; aryl or heteroaryl, in each case mono- or poly-substituted or unsubstituted; or aryl, $C_{3-8}$-cycloalkyl or heteroaryl bonded via $C_{1-3}$-alkyl, in each case mono- or poly-substituted or unsubstituted;

$R^9$ represents $OR^{11}$, $C_{1-5}$-alkyl, in each case saturated or unsaturated, branched or unbranched, mono- or poly-substituted or unsubstituted; $C_{3-8}$-cycloalkyl, in each case mono- or poly-substituted or unsubstituted; aryl or heteroaryl, in each case mono- or poly-substituted or unsubstituted; or aryl, $C_{3-8}$-cycloalkyl or heteroaryl bonded via $C_{1-3}$-alkyl, in each case mono- or poly-substituted or unsubstituted;

$R^{11}$ represents $C_{1-5}$-alkyl, in each case saturated or unsaturated, branched or unbranched, mono- or poly-substituted or unsubstituted; $C_{3-8}$-cycloalkyl, in each case mono- or poly-substituted or unsubstituted; aryl or heteroaryl, in each case mono- or poly-substituted or unsubstituted; or aryl, $C_{3-8}$-cycloalkyl or heteroaryl bonded via $C_{1-3}$-alkyl, in each case mono- or poly-substituted or unsubstituted;

or a physiologically acceptable salt thereof, and one or more physiologically acceptable auxiliary substances.

24. A method of treating pain in a mammal, said method comprising administering to said mammal an effective amount of a cyclohexyl-1,4-diamine compound corresponding to formula I

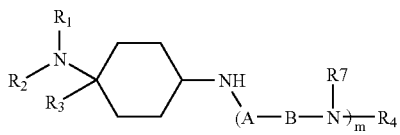

wherein $R^1$ and $R^2$, independently of one another, represent H; $C_{1-5}$-alkyl, in each case saturated or unsaturated, branched or unbranched, mono- or poly-substituted or unsubstituted; $C_{3-8}$-cycloalkyl, in each case mono- or poly-substituted or unsubstituted; or aryl, $C_{3-8}$-cycloalkyl or heteroaryl bonded via $C_{1-3}$-alkyl, in each case mono- or poly-substituted or unsubstituted;

or $R^1$ and $R^2$ together represent $CH_2CH_2OCH_2CH_2$, $CH_2CH_2NR^{10}CH_2CH_2$ or $(CH_2)_{3-6}$, wherein $R^{10}$ represents H; $C_{1-5}$-alkyl, in each case saturated or unsaturated, branched or unbranched, mono- or poly-substituted or unsubstituted; $C_{3-8}$-cycloalkyl, in each case mono- or poly-substituted or unsubstituted; aryl or heteroaryl, in each case mono- or poly-substituted or unsubstituted; or aryl, $C_{3-8}$-cycloalkyl or heteroaryl bonded via $C_{1-3}$-alkyl, in each case mono- or poly-substituted or unsubstituted; C(O)phenyl, C(O)heteroaryl, $C(O)C_{1-5}$-alkyl, in each case substituted or unsubstituted;

$R^3$ represents $C_{1-5}$-alkyl, in each case saturated or unsaturated, branched or unbranched, mono- or poly-substituted or unsubstituted; $C_{3-8}$-cycloalkyl, in each case mono- or poly-substituted or unsubstituted; aryl or heteroaryl, in each case unsubstituted or mono- or poly-substituted; aryl, heteroaryl or $C_{3-8}$-cycloalkyl bonded via a $C_{1-3}$-alkyl group, in each case unsubstituted or mono- or poly-substituted;

m represents 1, 2 or 3;

A represents C(O) or $SO_2$;

each B independently represents $(CR^5R^6)_n$, or aryl, heteroaryl or $C_{3-8}$-cycloalkyl, in each case mono- or poly-substituted or unsubstituted; or aryl, $C_{3-8}$-cycloalkyl or heteroaryl bonded via $C_{1-3}$-alkyl, wherein an individual carbon atom of the $C_{1-3}$-alkyl may be replaced by O, in each case mono- or poly-substituted or unsubstituted, wherein one $C_{1-3}$-alkyl may link the aryl, $C_{3-8}$-cycloalkyl or heteroaryl to A and N, or a first $C_{1-3}$-alkyl may link the aryl, $C_{3-8}$-cycloalkyl or heteroaryl to A and a second $C_{1-3}$-alkyl may link the aryl, $C_{3-8}$-cycloalkyl or heteroaryl to N; where n=1, 2, 3, 4 or 5:

$R^4$ represents $C(O)R^9$ or $SO_2R^8$;

$R^5$ and $R^6$ independently represent H, $C_{1-5}$-alkyl, in each case saturated or unsaturated, branched or unbranched, mono- or poly-substituted or unsubstituted; $C_{3-8}$-cycloalkyl, in each case mono- or poly-substituted or unsubstituted; aryl or heteroaryl, in each case mono- or poly-substituted or unsubstituted; or aryl, $C_{3-8}$-cycloalkyl or heteroaryl bonded via $C_{1-3}$-alkyl, in each case mono- or poly-substituted or unsubstituted;

$R^7$ represents H or, with B, forms a five-, six- or seven-membered ring which may be saturated or unsaturated but not aromatic and which may be part of a polycyclic system;

$R^8$ represents $C_{1-5}$-alkyl, in each case saturated or unsaturated, branched or unbranched, mono- or poly-substituted or unsubstituted; $C_{3-8}$-cycloalkyl, in each case mono- or poly-substituted or unsubstituted; aryl or heteroaryl, in each case mono- or poly-substituted or unsubstituted; or aryl, $C_{3-8}$-cycloalkyl or heteroaryl bonded via $C_{1-3}$-alkyl, in each case mono- or poly-substituted or unsubstituted;

$R^9$ represents $OR^{11}$, $C_{1-5}$-alkyl, in each case saturated or unsaturated, branched or unbranched, mono- or poly-substituted or unsubstituted; $C_{3-8}$-cycloalkyl, in each case mono- or poly-substituted or unsubstituted; aryl or heteroaryl, in each case mono- or poly-substituted or unsubstituted; or aryl, $C_{3-8}$-cycloalkyl or heteroaryl bonded via $C_{1-3}$-alkyl, in each case mono- or poly-substituted or unsubstituted;

$R^{11}$ represents $C_{1-5}$-alkyl, in each case saturated or unsaturated, branched or unbranched, mono- or poly-substituted or unsubstituted; $C_{3-8}$-cycloalkyl, in each case mono- or poly-substituted or unsubstituted; aryl or heteroaryl, in each case mono- or poly-substituted or unsubstituted; or aryl, $C_{3-8}$-cycloalkyl or heteroaryl bonded via $C_{1-3}$-alkyl, in each case mono- or poly-substituted or unsubstituted;

or a physiologically acceptable salt thereof.

25. The method of claim 24, wherein said pain is acute, neuropathic or chronic pain.

26. A method of treating a condition selected from the group consisting of anxiety, stress and stress-related syndromes, depression, epilepsy, Alzheimer's disease, senile dementia, catalepsy, general cognitive dysfunction, learning and memory disorders, withdrawal symptoms, alcohol abuse or dependency, drug abuse or dependency, medicine abuse or dependency, sexual dysfunction, cardiovascular disease, hypotension, hypertension, tinnitus, pruritus, migraine, hearing difficulties, deficient intestinal motility, impaired nutrient absorption, anorexia, obesity, locomotive disorders, diarrhea, cachexia, urinary incontinence, or providing a muscle relaxant, nootropic, anti-convulsive or anaesthetic or for co-administration in treatment with an opioid analgesic or anaesthetic, for diuresis or anti-natriuresis, anxiolysis, for modulation of motor activity, for modulation of neurotransmitter release and treatment of neurodegenerative diseases associated therewith, for the treatment of withdrawal symptoms or for reducing opioid addiction potential, said method comprising administering to a subject in need thereof a pharmaceutically effective amount of a cyclohexyl-1,4-diamine compound corresponding to formula I

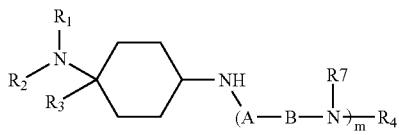

wherein $R^1$ and $R^2$, independently of one another, represent H; $C_{1-5}$-alkyl, in each case saturated or unsaturated, branched or unbranched, mono- or poly-substituted or unsubstituted; $C_{3-8}$-cycloalkyl, in each case mono- or poly-substituted or unsubstituted; or aryl, $C_{3-8}$-cycloalkyl or heteroaryl bonded via $C_{1-3}$-alkyl, in each case mono- or poly-substituted or unsubstituted;

or $R^1$ and $R^2$ together represent $CH_2CH_2OCH_2CH_2$, $CH_2CH_2NR^{10}CH_2CH_2$ or $(CH_2)_{3-6}$, wherein $R^{10}$ represents H; $C_{1-5}$-alkyl, in each case saturated or unsaturated, branched or unbranched, mono- or poly-substituted or unsubstituted; $C_{3-8}$-cycloalkyl, in each case mono- or poly-substituted or unsubstituted; aryl or heteroaryl, in each case mono- or poly-substituted or unsubstituted; or aryl, $C_{3-8}$-cycloalkyl or heteroaryl bonded via $C_{1-3}$-alkyl, in each case mono- or poly-substituted or unsubstituted; C(O)phenyl, C(O)heteroaryl, $C(O)C_{1-5}$-alkyl, in each case substituted or unsubstituted;

$R^3$ represents $C_{1-5}$-alkyl, in each case saturated or unsaturated, branched or unbranched, mono- or poly-substituted or unsubstituted; $C_{3-8}$-cycloalkyl, in each case mono- or poly-substituted or unsubstituted; aryl or heteroaryl, in each case unsubstituted or mono- or poly-substituted; aryl, heteroaryl or $C_{3-8}$-cycloalkyl bonded via a $C_{1-3}$-alkyl group, in each case unsubstituted or mono- or poly-substituted;

m represents 1, 2 or 3;

A represents C(O) or $SO_2$;

each B independently represents $(CR^5R^6)_n$ or aryl, heteroaryl or $C_{3-8}$-cycloalkyl, in each case mono- or poly-substituted or unsubstituted; or aryl, $C_{3-8}$-cycloalkyl or heteroaryl bonded via $C_{1-3}$-alkyl, wherein an individual carbon atom of the $C_{1-3}$-alkyl may be replaced by O, in each case mono- or poly-substituted or unsubstituted, wherein one $C_{1-3}$-alkyl may link the aryl, $C_{3-8}$-cycloalkyl or heteroaryl to A and N, or a first $C_{1-3}$-alkyl may link the aryl, $C_{3-8}$-cycloalkyl or heteroaryl to A and a second $C_{1-3}$-alkyl may link the aryl, $C_{3-8}$-cycloalkyl or heteroaryl to N; where n=1, 2, 3, 4 or 5;

$R^4$ represents $C(O)R^9$ or $SO_2R^8$;

$R^5$ and $R^6$ independently represent H, $C_{1-5}$-alkyl, in each case saturated or unsaturated, branched or unbranched, mono- or poly-substituted or unsubstituted; $C_{3-8}$-cycloalkyl, in each case mono- or poly-substituted or unsubstituted; aryl or heteroaryl, in each case mono- or poly-substituted or unsubstituted; or aryl, $C_{3-8}$-cycloalkyl or heteroaryl bonded via $C_{1-3}$-alkyl, in each case mono- or poly-substituted or unsubstituted;

$R^7$ represents H or, with B, forms a five-, six- or seven-membered ring which may be saturated or unsaturated but not aromatic and which may be part of a polycyclic system;

$R^8$ represents $C_{1-5}$-alkyl, in each case saturated or unsaturated, branched or unbranched, mono- or poly-substituted or unsubstituted; $C_{3-8}$-cycloalkyl, in each case mono- or poly-substituted or unsubstituted; aryl or heteroaryl, in each case mono- or poly-substituted or unsubstituted; or aryl, $C_{3-8}$-cycloalkyl or heteroaryl bonded via $C_{1-3}$-alkyl, in each case mono- or poly-substituted or unsubstituted;

$R^9$ represents $OR^{11}$, $C_{1-5}$-alkyl, in each case saturated or unsaturated, branched or unbranched, mono- or poly-substituted or unsubstituted; $C_{3-8}$-cycloalkyl, in each case mono- or poly-substituted or unsubstituted; aryl or heteroaryl, in each case mono- or poly-substituted or unsubstituted; or aryl, $C_{3-8}$-cycloalkyl or heteroaryl bonded via $C_{1-3}$-alkyl, in each case mono- or poly-substituted or unsubstituted;

$R^{11}$ represents $C_{1-5}$-alkyl, in each case saturated or unsaturated, branched or unbranched, mono- or poly-substituted or unsubstituted; $C_{3-8}$-cycloalkyl, in each case mono- or poly-substituted or unsubstituted; aryl or heteroaryl, in each case mono- or poly-substituted or unsubstituted; or aryl, $C_{3-8}$-cycloalkyl or heteroaryl bonded via $C_{1-3}$-alkyl, in each case mono- or poly-substituted or unsubstituted;

or a physiologically acceptable salt thereof.

27. A cyclohexyl-1,4-diamine compound corresponding to formula I

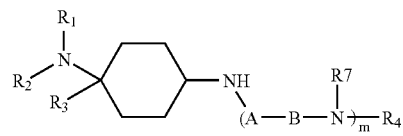

wherein $R^1$ and $R^2$, independently of one another, represent H; $C_{1-5}$-alkyl, in each case saturated or unsaturated, branched or unbranched, mono- or poly-substituted or unsubstituted; $C_{3-8}$-cycloalkyl, in each case mono- or poly-substituted or unsubstituted; or aryl, $C_{3-8}$-cycloalkyl or heteroaryl bonded via $C_{1-3}$-alkyl, in each case mono- or poly-substituted or unsubstituted;

or $R^1$ and $R^2$ together represent $CH_2CH_2OCH_2CH_2$, $CH_2CH_2NR^{10}CH_2CH_2$ or $(CH_2)_{3-6}$, wherein $R^{10}$ represents H; $C_{1-5}$-alkyl, in each case saturated or unsaturated, branched or unbranched, mono- or poly-substituted or unsubstituted; $C_{3-8}$-cycloalkyl, in each case mono- or poly-substituted or unsubstituted; aryl or heteroaryl, in each case mono- or poly-substituted or unsubstituted; or aryl, $C_{3-8}$-cycloalkyl or heteroaryl bonded via $C_{1-3}$-alkyl, in each case mono- or poly-substituted or unsubstituted; C(O)phenyl, C(O)heteroaryl, $C(O)C_{1-5}$-alkyl, in each case substituted or unsubstituted;

$R^3$ represents $C_{1-5}$-alkyl, in each case saturated or unsaturated, branched or unbranched, mono- or poly-substituted or unsubstituted; $C_{3-8}$-cycloalkyl, in each case mono- or poly-substituted or unsubstituted; aryl or heteroaryl, in each case unsubstituted or mono- or polysubstituted; aryl, heteroaryl or $C_{3-8}$-cycloalkyl bonded via a $C_{1-3}$-alkyl group, in each case unsubstituted or mono- or poly-substituted;

m represents 1, 2 or 3;

A represents C(O) or $SO_2$;

each B independently represents $(CR^5R^6)_n$ or aryl, heteroaryl or $C_{3-8}$-cycloalkyl, in each case mono- or poly-substituted or unsubstituted; or aryl, $C_{3-8}$-cycloalkyl or heteroaryl bonded via $C_{1-3}$-alkyl, wherein an individual carbon atom of the $C_{1-3}$-alkyl may be replaced by O, in each case mono- or poly-substituted or unsubstituted, wherein one $C_{1-3}$-alkyl may link the aryl, $C_{3-8}$-cycloalkyl or heteroaryl to A and N, or a first $C_{1-3}$-alkyl may link the aryl, $C_{3-8}$-cycloalkyl or heteroaryl to A and a second $C_{1-3}$-alkyl may link the aryl, $C_{3-8}$-cycloalkyl or heteroaryl to N; where n=1, 2, 3, 4 or 5;

$R^4$ represents $C(O)R^9$ or $SO_2R^8$;

$R^5$ and $R^6$ independently represent H, $C_{1-5}$-alkyl, in each case saturated or unsaturated, branched or unbranched, mono- or poly-substituted or unsubstituted; $C_{3-8}$-cycloalkyl, in each case mono- or poly-substituted or unsubstituted; aryl or heteroaryl, in each case mono- or poly-substituted or unsubstituted; or aryl, $C_{3-8}$-cycloalkyl or heteroaryl bonded via $C_{1-3}$-alkyl, in each case mono- or poly-substituted or unsubstituted;

$R^7$ represents H or, with B, forms a five-, six- or seven-membered ring which may be saturated or unsaturated but not aromatic and which may be part of a polycyclic system;

$R^8$ represents $C_{1-5}$-alkyl, in each case saturated or unsaturated, branched or unbranched, mono- or poly-substituted or unsubstituted; $C_{3-8}$-cycloalkyl, in each case mono- or poly-substituted or unsubstituted; aryl or heteroaryl, in each case mono- or poly-substituted or unsubstituted; or aryl, $C_{3-8}$-cycloalkyl or heteroaryl bonded via $C_{1-3}$-alkyl, in each case mono- or poly-substituted or unsubstituted;

$R^9$ represents $OR^{11}$, $C_{1-5}$-alkyl, in each case saturated or unsaturated, branched or unbranched, mono- or poly-substituted or unsubstituted; $C_{3-8}$-cycloalkyl, in each case mono- or poly-substituted or unsubstituted; aryl or heteroaryl, in each case mono- or poly-substituted or unsubstituted; or aryl, $C_{3-8}$-cycloalkyl or heteroaryl bonded via $C_{1-3}$-alkyl, in each case mono- or poly-substituted or unsubstituted;

$R^{11}$ represents $C_{1-5}$-alkyl, in each case saturated or unsaturated, branched or unbranched, mono- or poly-substituted or unsubstituted; $C_{3-8}$-cycloalkyl, in each case mono- or poly-substituted or unsubstituted; aryl or heteroaryl, in each case mono- or poly-substituted or unsubstituted; or aryl, $C_{3-8}$-cycloalkyl or heteroaryl bonded via $C_{1-3}$-alkyl, in each case mono- or poly-substituted or unsubstituted;

or an acid, base, solvate or a physiologically acceptable salt thereof.

28. The compound of claim 27, wherein said compound is present in the form of a hydrate.

29. A cyclohexyl-1,4-diamine compound according to claim 9, wherein $R^3$ represents phenyl, pyridyl, thiophenyl, 4-chlorobenzyl, benzyl, 3-fluorophenyl, 3-chlorobenzyl, 4-methylbenzyl, 2-chlorobenzyl, 4-fluorobenzyl, 3-methylbenzyl, 2-methylbenzyl, 3-fluorobenzyl, 2-fluorobenzyl or phenethyl.

30. A cyclohexyl-1,4-diamine compound according to claim 1, wherein $R^4$ represents $C(O)R^9$, and $R^9$ represents $OR^{11}$, $C_{1-5}$-alkyl, cyclohexyl, cyclopentyl, cyclobutyl, cycloheptyl, cyclooctyl, phenyl, benzyl, naphthyl, thiophenyl, benzothiophenyl, furanyl, pyrazolyl, benzofuranyl, benzodioxolanyl, isoquinolinyl, indolyl, pyrrolyl, pyridyl, pyrimidyl or pyrazinyl, in each case unsubstituted or mono- or poly-substituted; phenyl, naphthyl, thiophenyl, benzothiophenyl, pyridyl, furyl, benzofuranyl, indolyl, benzodioxanyl, pyrrolyl, pyrimidyl or pyrazinyl bonded via a saturated, unbranched substituted or unsubstituted $C_{1-2}$-alkyl group, in each case unsubstituted or mono- or poly-substituted.

31. A cyclohexyl-1,4-diamine compound according to claim 1, wherein $R^4$ represents $C(O)R^9$, and $R^9$ represents $OR^{11}$, phenyl, $C_{1-5}$-alkyl, branched or unbranched, saturated or unsaturated, or benzyl, in each case unsubstituted or mono- or poly-substituted.

* * * * *